United States Patent
Minekawa et al.

(10) Patent No.: US 10,436,576 B2
(45) Date of Patent: Oct. 8, 2019

(54) DEFECT REVIEWING METHOD AND DEVICE

(71) Applicant: HITACHI HIGH-TECHNOLOGIES CORPORATION, Tokyo (JP)

(72) Inventors: Yohei Minekawa, Tokyo (JP); Yuko Otani, Tokyo (JP); Yuji Takagi, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/126,391

(22) PCT Filed: Mar. 19, 2015

(86) PCT No.: PCT/JP2015/058233
§ 371 (c)(1),
(2) Date: Sep. 15, 2016

(87) PCT Pub. No.: WO2015/159641
PCT Pub. Date: Oct. 22, 2015

(65) Prior Publication Data
US 2017/0082425 A1 Mar. 23, 2017

(30) Foreign Application Priority Data
Apr. 18, 2014 (JP) .................................. 2014-086395

(51) Int. Cl.
*G01B 11/14* (2006.01)
*G02B 21/36* (2006.01)
(Continued)

(52) U.S. Cl.
CPC .............. *G01B 11/14* (2013.01); *G01B 11/30* (2013.01); *G01N 21/9501* (2013.01);
(Continued)

(58) Field of Classification Search
CPC ...... G01B 11/14; G01B 11/30; G01N 21/956; G02B 21/0092; G02B 21/10
See application file for complete search history.

(56) References Cited

U.S. PATENT DOCUMENTS 9,436,990 B2 * 9/2016 Otani ................. G02B 21/0004
9,683,946 B2 * 6/2017 Otani ................. G01N 21/9501
(Continued)

FOREIGN PATENT DOCUMENTS

JP         09-061367 A    3/1997
JP      2009-042040 A    2/2009
(Continued)

*Primary Examiner* — Violeta A Prieto
(74) *Attorney, Agent, or Firm* — Volpe and Koenig, P.C.

(57) ABSTRACT

To review minute defects that were buried in roughness scattered light with an observation device provided with a dark-field microscope, a scanning electron microscope (SEM), and a control unit, the present invention configures the dark-field microscope by installing a filter for blocking a portion of the scattered light, an imaging lens for focusing the scattered light that has passed through the filter, and a detector for dividing the image of the scattered light focused by the imaging lens into the polarization directions converted by a wavelength plate and detecting the resulting images, and the control has a calculation unit for determining the position of a defect candidate detected by another inspection device using the plurality of images separated into polarization directions and detected by the detector.

4 Claims, 19 Drawing Sheets

(51) Int. Cl.
*G02B 21/10* (2006.01)
*G02B 21/00* (2006.01)
*G01N 23/2251* (2018.01)
*G01N 23/2204* (2018.01)
*G01B 11/30* (2006.01)
*G01N 21/956* (2006.01)
*G01N 21/95* (2006.01)
*G02B 5/30* (2006.01)
*G01N 21/88* (2006.01)

(52) U.S. Cl.
CPC ....... *G01N 21/956* (2013.01); *G01N 23/2204* (2013.01); *G02B 21/0092* (2013.01); *G02B 21/10* (2013.01); *G01N 23/2251* (2013.01); *G01N 2021/8848* (2013.01); *G01N 2223/30* (2013.01); *G01N 2223/646* (2013.01); *G02B 5/3083* (2013.01); *G02B 21/361* (2013.01); *G02B 21/367* (2013.01)

(56) References Cited

U.S. PATENT DOCUMENTS

| | | | |
|---|---|---|---|
| 9,773,641 B2* | 9/2017 | Otani | ............... H01J 37/261 |
| 2012/0274931 A1 | 11/2012 | Otani et al. | |
| 2013/0027557 A1* | 1/2013 | Hirai | ............... B60S 1/0844 |
| | | | 348/148 |
| 2013/0250297 A1 | 9/2013 | Ito et al. | |
| 2013/0277553 A1* | 10/2013 | Otani | ............... G01N 21/8806 |
| | | | 250/307 |
| 2015/0003722 A1* | 1/2015 | Otani | ............... G02B 21/0004 |
| | | | 382/149 |
| 2015/0276622 A1* | 10/2015 | Otani | ............... G01N 21/9501 |
| | | | 356/237.5 |

FOREIGN PATENT DOCUMENTS

| | | | | |
|---|---|---|---|---|
| JP | 2011-106974 A | 6/2011 | | |
| JP | 2012-026733 A | 2/2012 | | |
| JP | 2012-117852 A | 6/2012 | | |
| JP | WO 2013118351 A1 * | 8/2013 | ......... | G02B 21/0004 |

* cited by examiner

F I G. 1
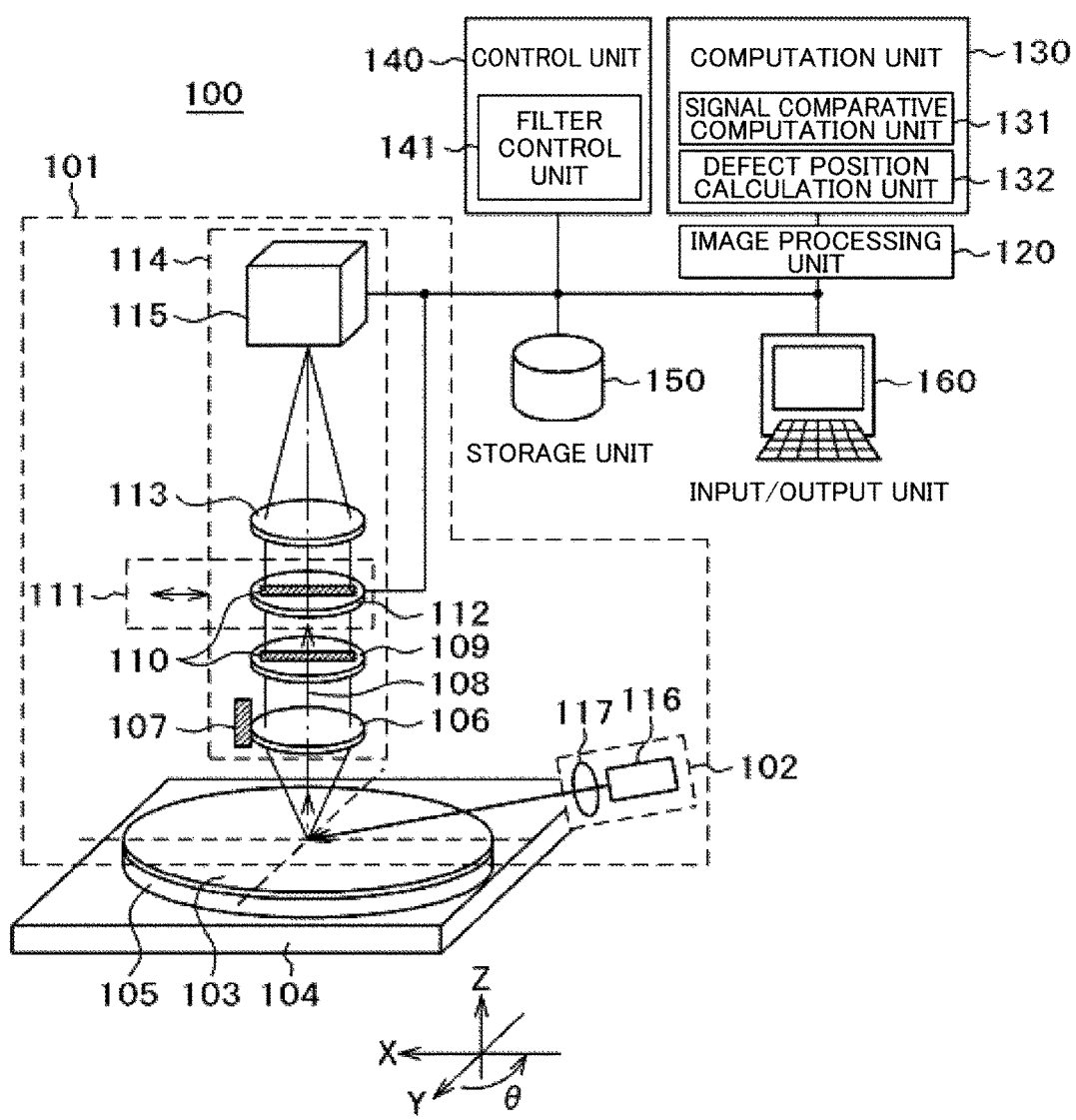

ROUGHNESS

RADIALLY POLARIZED LIGHT

ROUGHNESS

AZIMUTHALLY POLARIZED LIGHT

TINY FOREIGN MATTER

RADIALLY POLARIZED LIGHT

FIG. 3D
TINY FOREIGN MATTER
AZIMUTHALLY POLARIZED LIGHT
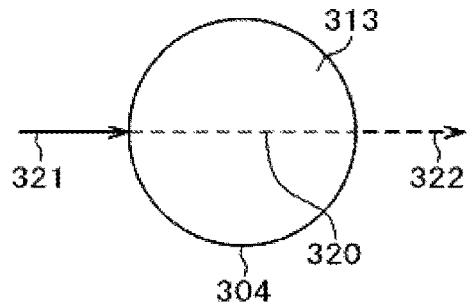
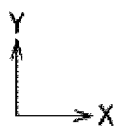
FIG. 4A
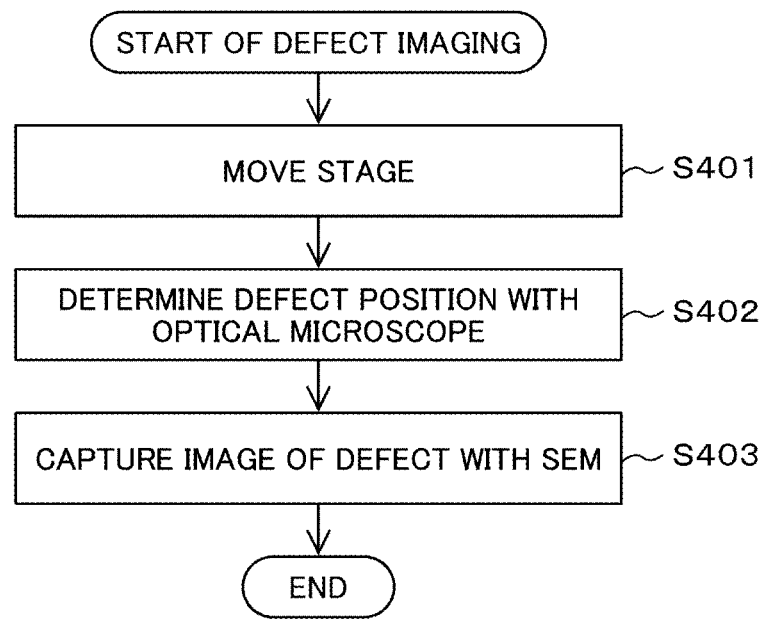

F I G. 5B
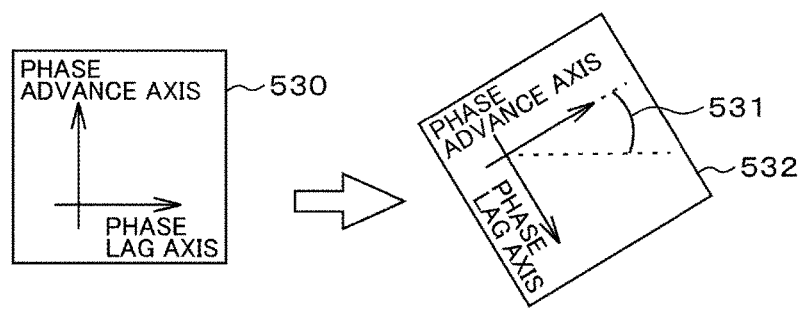
F I G. 5C
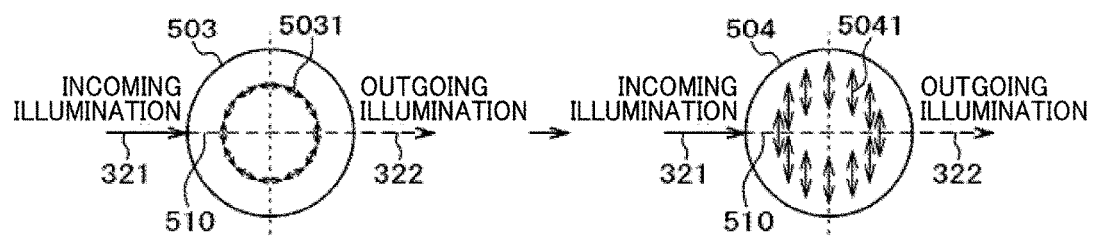

F I G. 7 A
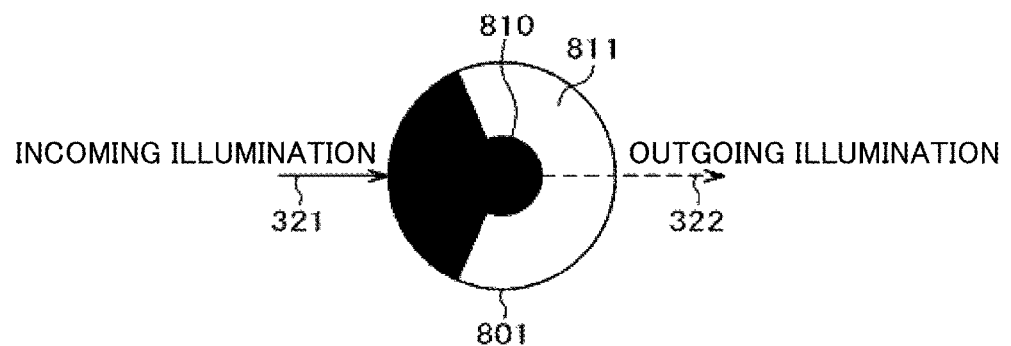
F I G. 7 B
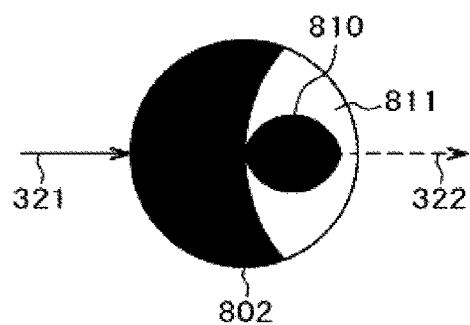

F I G. 8 A
RADIALLY POLARIZED LIGHT
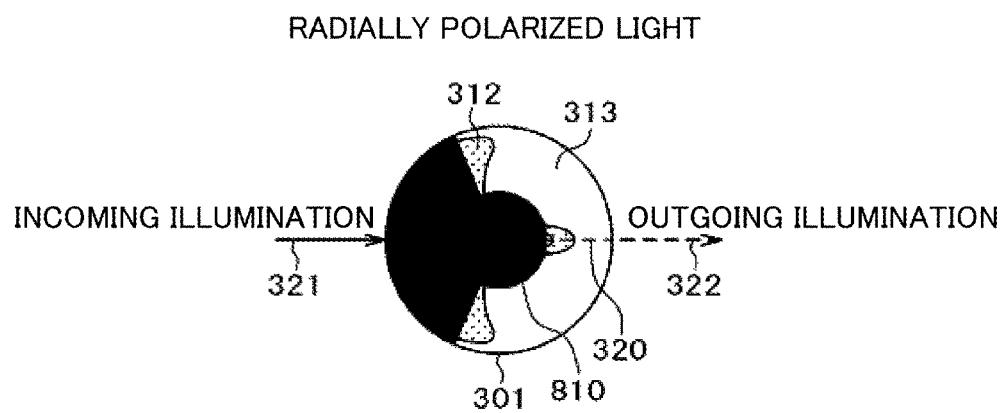
F I G. 8 B
RADIALLY POLARIZED LIGHT
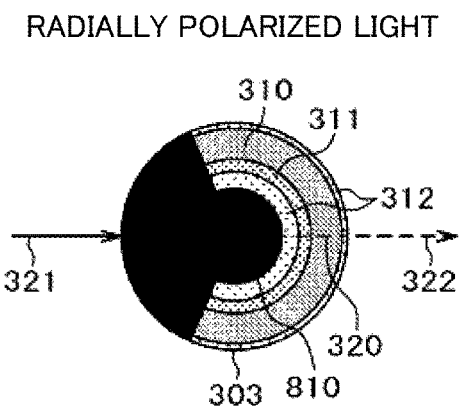

F I G. 1 1
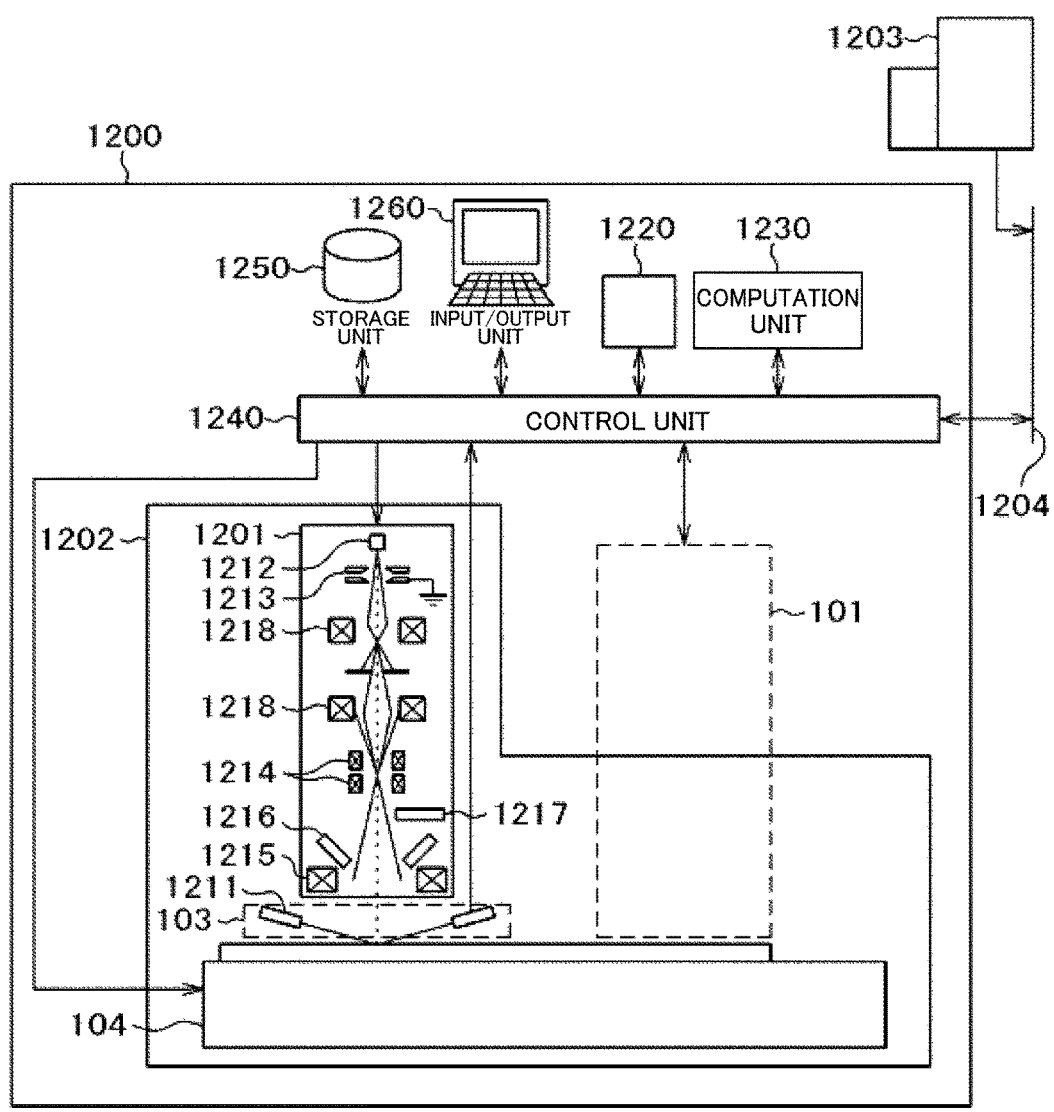

F I G. 1 2 A
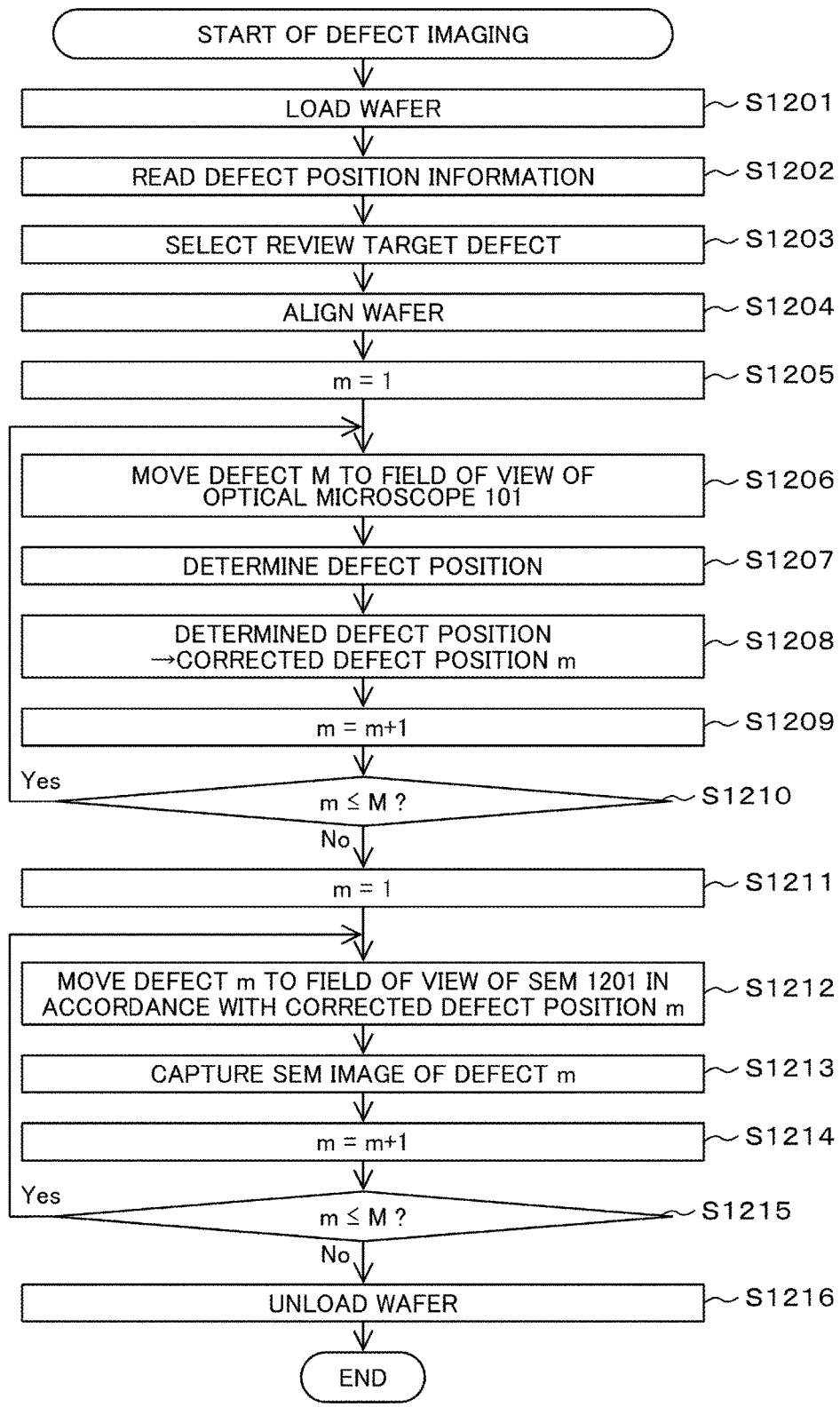

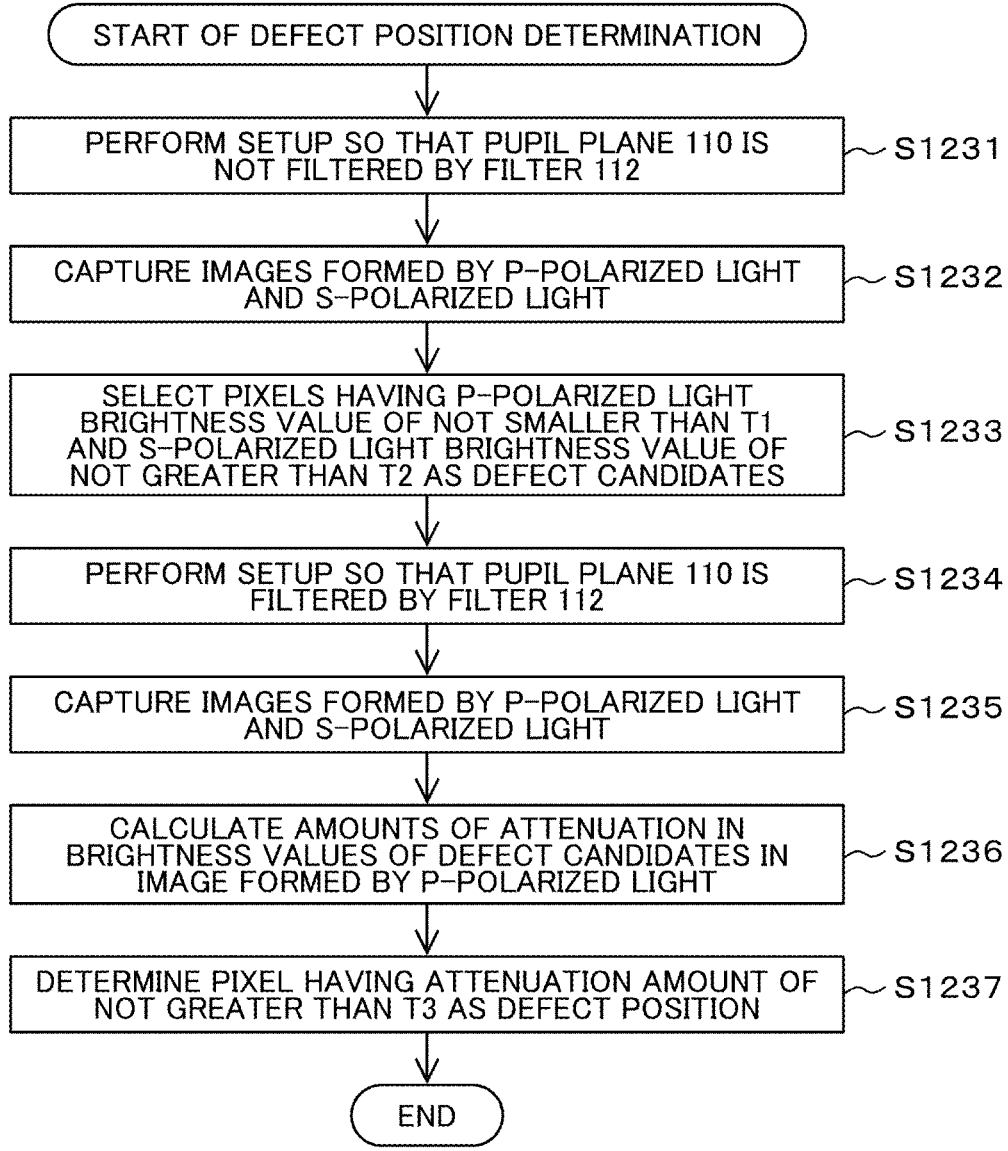
F I G. 1 2 B

F I G. 1 3
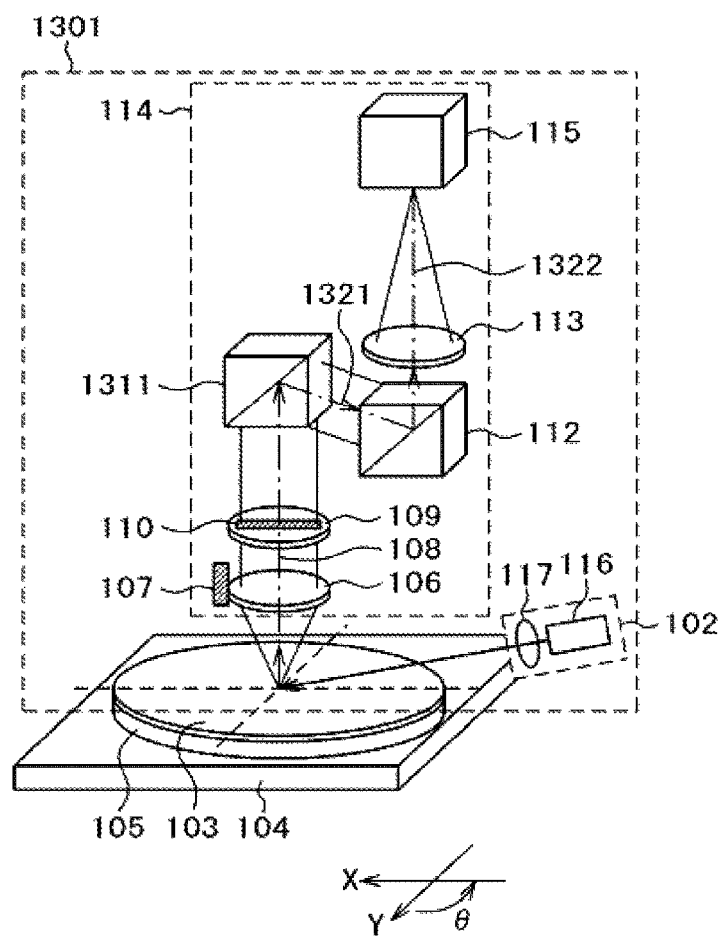

F I G. 1 4
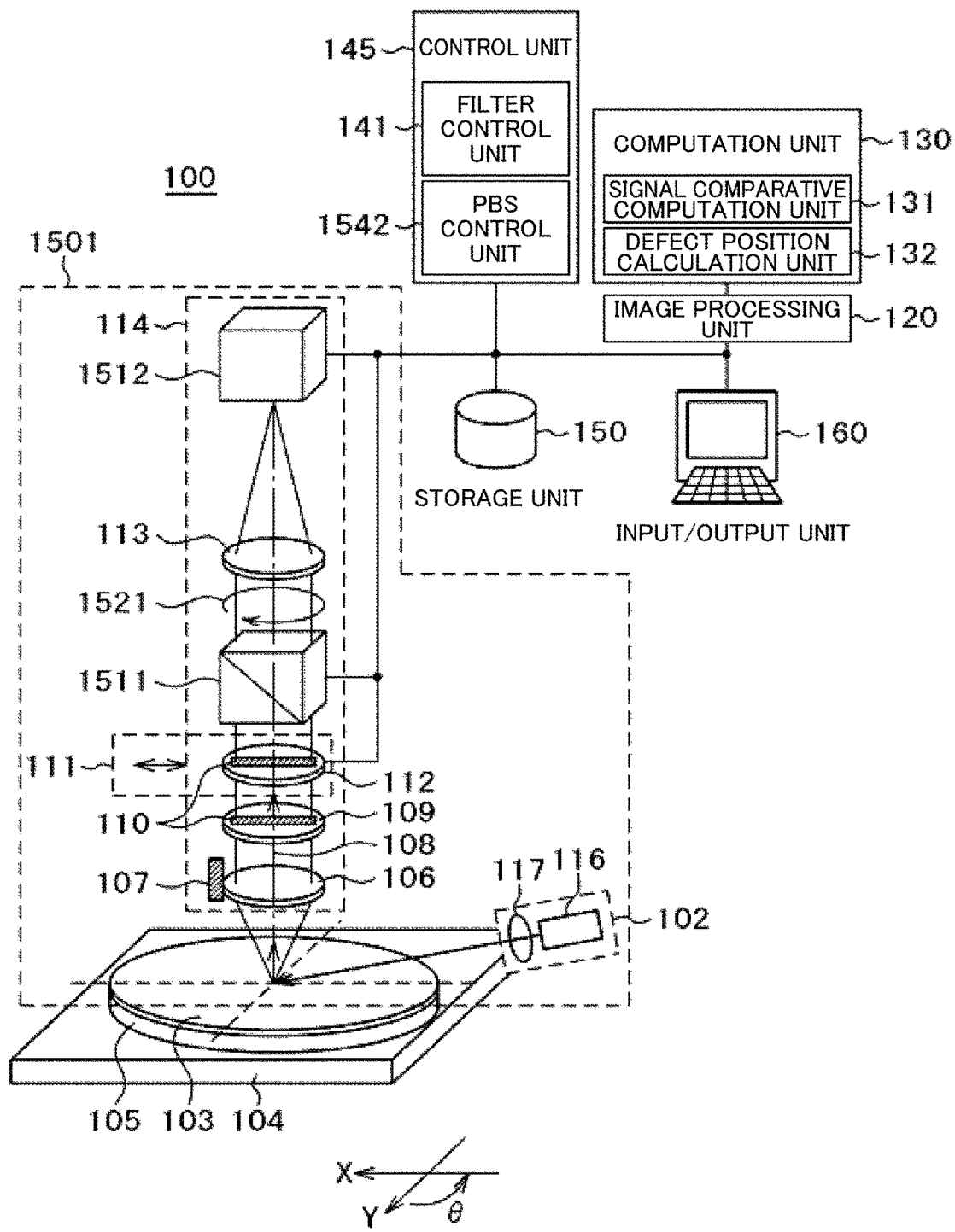

DEFECT REVIEWING METHOD AND DEVICE

TECHNICAL FIELD

The present invention relates to a defect reviewing method of reviewing, for example, a defect existing on a sample surface or in the vicinity of the sample surface, which is detected by a defect inspection device. The present invention further relates to a defect coordinate derivation method. The present invention still further relates to a defect reviewing device and a defect coordinate derivation device.

As regards LSI manufacture in recent years, defects to be reviewed are miniaturized because circuit patterns are miniaturized in response to a need for high integration. Thus, defects to be re-detected by an optical microscope are also miniaturized. In order to review the details of defects on a semiconductor wafer with a defect reviewing device formed of a scanning electron microscope (SEM), it is necessary to capture an image while foreign matter or a pattern defect such as a short-circuited or open-circuited pattern (hereinafter generically referred to as defects) is positioned within the field of view (FOV) of the SEM in accordance with position information obtained from a defect inspection device. If, in this instance, the accuracy of position detection by the inspection device is low or the SEM and the inspection device significantly differ in reference coordinates, a defect may not always be positioned within the FOV of the SEM. Therefore, a position on a sample is re-detected with an optical microscope mounted in an SEM defect reviewing device by using position information about a defect on a sample, which is detected by the inspection device. The position information about the defect, which is detected by the inspection device, is then corrected to capture an image of the defect with an SEM.

An optical microscope used to re-detect a position on a sample for the purpose of reviewing a defect with an SEM illuminates the surface of a semiconductor wafer with a laser in order to locate a defect through dark-field observation of light scattered from the defect. Scattering from an object having a wavelength sufficiently smaller than an illumination wavelength is Rayleigh scattering, which is proportional to the sixth power of the particle diameter of a scatterer. Therefore, when the defect size of a measurement target decreases, the intensity of defect scattered light may drastically decrease to obscure Rayleigh scattering by roughness scattered light, that is, light scattered from a rough sample surface. Even if high-intensity illumination is used to increase a storage time for the purpose of increasing the intensity of defect scattered light, an adequate defect scattered light intensity for separating the roughness scattered light from the defect is not obtained due to a decrease in the defect size. Thus, the defect is obscured by the roughness scattered light and cannot be properly detected. Consequently, the position of the defect is not accurately determined so that the defect cannot be positioned within the FOV of the SEM. This results in the inability to review the details of the defect.

A method of separating defect scattered light from roughness scattered light is described in Patent Literature 1. This method makes use of intensity distribution difference in a particular polarization direction of scattered light, or more specifically, selectively transmits the defect scattered light through a filter (mask, polarizer, or distribution wavelength plate) disposed on a pupil plane in order to make the defect scattered light distinct from the roughness scattered light.

Another method of separating defect scattered light from roughness scattered light is described in Patent Literature 2. This method makes use of scattered light intensity difference in a particular polarization direction, or more specifically, makes the defect scattered light distinct from the roughness scattered light by separating multiple scattered light beams having different polarization directions and comparing the scattered light intensities in the polarization directions detected separately by multiple detectors.

CITATION LIST

Patent Literature

PTL 1: Japanese Patent Application Laid-Open Publication No. 2011-106974
PTL 2: Japanese Patent Application Laid-Open Publication No. 2012-026733

SUMMARY OF INVENTION

Technical Problem

The method of separating defect scattered light from wafer roughness scattered light, which is described in Patent Literature 1, makes use of intensity distribution difference in a particular polarization direction of scattered light. More specifically, this method selectively transmits the defect scattered light through a filter (mask, polarizer, or distribution wavelength plate) disposed on a pupil plane in order to make the defect scattered light distinct from the roughness scattered light. However, the roughness scattered light is not completely blocked by the filter. The roughness scattered light outside a filtering range is detected by a detector. Further, the scattered light intensity of the defect scattered light decreases with a decrease in the defect size. Therefore, when the intensity of the defect scattered light decreases due, for instance, to a decrease in the defect size so as to reduce the intensity difference between the defect scattered light and the roughness scattered light outside the filtering range, the defect scattered light may be obscured by the roughness scattered light and rendered undetectable.

Meanwhile, the other method of separating defect scattered light from roughness scattered light, which is described in Patent Literature 2, makes use of scattered light intensity difference in a particular polarization direction. More specifically, this method makes the defect scattered light distinct from the roughness scattered light by separating multiple scattered light beams having different polarization directions and comparing the scattered light intensities in the polarization directions detected separately by multiple detectors. However, in order to make the defect scattered light distinct, it is necessary to compare the scattered light intensities at spatially the same or nearby positions of images formed in various polarization directions, which are captured separately by the multiple detectors. Yet, this method uses the multiple detectors to separately capture images formed in various polarization directions. Therefore, the spatial correspondence between pixels is not guaranteed for the images formed in various polarization directions. Consequently, it is not possible to compare the scattered light intensities at spatially the same or nearby positions of images formed in various polarization directions. This may result in the inability to make the defect scattered light distinct.

The present invention has been made to address the above-described prior-art problems. In a situation where minute defects, which are previously obscured by roughness scattered light and undetectable, are made distinct, and the details of defects detected by an optical defect detection device are reviewed, for example, with an SEM, the present invention provides a defect reviewing method and device that make it possible to efficiently review minute defects by surely positioning a minute defect targeted for a review within the observation field of view, for example, of the SEM.

Solution to Problem

In order to address the above-described problem, according to a first aspect of the present invention, there is provided a defect reviewing device including a dark-field microscope, a SEM (scanning electron microscope), a table, and a control unit. The dark-field microscope identifies a position of a defect on a sample that is detected by another inspection device. The SEM reviews the defect on the sample the position of which is identified by the dark-field microscope. The table on which the sample is mounted is capable of moving between the dark-field microscope and the SEM. The control unit controls the dark-field microscope, the SEM, and the table. The dark-field microscope includes an illumination light source, an objective lens, a wavelength plate, a filter, an imaging lens, and a detector. The illumination light source illuminates the sample with illumination light. The objective lens collects scattered light generated from the sample that is illuminated with the illumination light from the illumination light source. The wavelength plate converts the polarization directions of the scattered light from the sample, which is collected by the objective lens. The filter blocks part of the scattered light transmitted through the wavelength plate and transmits the remaining portion of the scattered light. The imaging lens forms an image of the scattered light transmitted through the filter. The detector detects the image of the scattered light, which is formed by the imaging lens, by separating the image into the polarization directions converted by the wavelength plate. The control unit includes a computation unit. The computation unit determines the position of a defect candidate detected by the other inspection device by using multiple images that are detected by the detector after separation into the polarization directions.

In order to address the above-described problem, according to a second aspect of the present invention, there is provided a defect reviewing device including a dark-field microscope, a SEM (scanning electron microscope), a table, and a control unit. The dark-field microscope identifies a position of a defect on a sample that is detected by another inspection device. The SEM reviews the defect on the sample the position of which is identified by the dark-field microscope. The table on which the sample is mounted is capable of moving between the dark-field microscope and the SEM. The control unit controls the dark-field microscope, the SEM, and the table. The dark-field microscope includes an illumination light source, an objective lens, a wavelength plate, a polarization beam splitter, an imaging lens, and a detector. The illumination light source illuminates the sample with illumination light. The objective lens collects scattered light generated from the sample that is illuminated with the illumination light from the illumination light source. The wavelength plate converts the polarization directions of the scattered light from the sample, which is collected by the objective lens. The polarization beam splitter is rotatable about the optical axis of the objective lens. The imaging lens forms an image of the scattered light transmitted through the polarization beam splitter. The detector detects the image of the scattered light that is formed by the imaging lens. The control unit includes a computation unit. The computation unit identifies a position of a defect candidate detected by the other inspection device by using multiple images that are detected with the detector by rotating the polarization beam splitter about the optical axis.

In order to address the above-described problem, according to a third aspect of the present invention, there is provided a defect reviewing device including a dark-field microscope, an SEM (scanning electron microscope), a table, and a control unit. The dark-field microscope identifies a position of a defect on a sample that is detected by another inspection device. The SEM reviews the defect on the sample the position of which is identified by the dark-field microscope. The table on which the sample is mounted is capable of moving between the dark-field microscope and the SEM. The control unit controls the dark-field microscope, the SEM, and the table. The dark-field microscope includes an illumination light source, an objective lens, a filter, an imaging lens, and a detector. The illumination light source illuminates the sample with illumination light. The objective lens collects scattered light generated from the sample that is illuminated with the illumination light from the illumination light source. The filter includes a light-shielding region for shielding part of the scattered light from the sample, which is collected by the objective lens, and is capable of changing the light-shielding region. The imaging lens forms an image of the scattered light transmitted through a portion other than the light-shielding region of the filter. The detector detects the image of the scattered light that is formed by the imaging lens. The control unit includes a computation unit. The computation unit determines the position of a defect candidate detected by the other inspection device by using multiple images that are detected with the detector by changing the light-shielding region of the filter.

In order to address the above-described problem, according to a fourth aspect of the present invention, there is provided a defect reviewing method including the steps of identifying a position of a defect on a sample, which is detected by another inspection device, by using an image captured by a dark-field microscope; and reviewing, with an SEM (scanning electron microscope), the defect on the sample the position of which is identified by the dark-field microscope. The step of capturing, with the dark-field microscope, an image indicative of the position of the defect on the sample, which is detected by the other inspection device includes the steps of collecting, with an objective lens, scattered light that is generated from the sample when the sample is illuminated with illumination light emitted from an illumination light source; converting the polarization direction of the scattered light by transmitting through a wavelength plate the scattered light from the sample, which is collected by the objective lens; allowing the scattered light transmitted through the wavelength plate to fall on a filter to block part of the scattered light and transmit the remaining portion of the scattered light; forming an image of the scattered light transmitted through the filter and detecting the image of the scattered light by separating the image into the polarization directions converted by the wavelength plate; and identifying a position of a defect candidate detected by the other inspection device by using multiple images that are detected after separation into the polarization directions.

In order to address the above-described problem, according to a fifth aspect of the present invention, there is provided a defect reviewing method including the steps of identifying a position of a defect on a sample, which is detected by another inspection device, by using an image captured by a dark-field microscope; and reviewing, with an SEM (scanning electron microscope), the defect on the sample the position of which is identified by the dark-field microscope. The step of capturing, with the dark-field microscope, an image indicative of the position of the defect on the sample, which is detected by the other inspection device includes the steps of collecting, with an objective lens, scattered light that is generated from the sample when the sample is illuminated with illumination light emitted from an illumination light source; converting the polarization direction of the scattered light by transmitting through a wavelength plate the scattered light from the sample, which is collected by the objective lens; performing multiple times, at various polarization beam splitter angles, a sequence of forming and detecting an image of the scattered light transmitted through a polarization beam splitter rotatable about the optical axis of the objective lens; and identifying a position of a defect candidate detected by the other inspection device by using multiple images that are detected and obtained multiple times at the various polarization beam splitter angles.

In order to address the above-described problem, according to a sixth aspect of the present invention, there is provided a defect reviewing method including the steps of identifying a position of a defect on a sample, which is detected by another inspection device, by using an image captured by a dark-field microscope; and reviewing, with an SEM (scanning electron microscope), the defect on the sample the position of which is identified by the dark-field microscope. The step of capturing, with the dark-field microscope, an image indicative of the position of the defect on the sample, which is detected by the other inspection device includes the steps of collecting, with an objective lens, scattered light that is generated from the sample when the sample is illuminated with illumination light emitted from an illumination light source; detecting multiple images by performing multiple times a sequence of forming and detecting an image of the scattered light from the sample, which is collected by the objective lens, by transmitting the scattered light through a filter having a variable light-shielding region while varying the light-shielding region; and identifying a position of a defect candidate detected by the other inspection device by using the multiple images that are detected while varying the light-shielding region of the filter.

Advantageous Effects of Invention

Minute defects that are previously obscured by roughness scattered light and undetectable can be made distinct by the present invention. In a situation where the details of defects detected by an optical defect inspection device are to be reviewed, for example, with an SEM, the present invention makes it possible to review minute defects by surely positioning a minute defect targeted for a review within the observation field of view, for example, of the SEM.

BRIEF DESCRIPTION OF DRAWINGS

FIG. 1 is a block diagram illustrating a schematic configuration of an optical microscope in accordance with an embodiment of the present invention.

FIG. 3D is a diagram illustrating the azimuthally polarized light intensity distribution of scattered light from minute foreign matter on a pupil plane.

FIG. 4A is a flowchart illustrating defect imaging steps according to an embodiment of the present invention.

FIG. 5B is a diagram illustrating the rotation of the polarization direction of a ½ wavelength plate in accordance with an embodiment of the present invention.

FIG. 5C is a diagram illustrating an example in which azimuthally polarized light is converted to P-polarized light on a pupil plane by using a distribution wavelength plate in accordance with an embodiment of the present invention.

FIG. 7A is a diagram illustrating an exemplary shape of a filter disposed on a pupil plane in accordance with an embodiment of the present invention.

FIG. 7B is a diagram illustrating an exemplary shape of the filter disposed on the pupil plane in accordance with an embodiment of the present invention.

FIG. 8A is a diagram illustrating the intensity distribution of radially polarized light generated due to roughness when a filter is disposed on the pupil plane in accordance with an embodiment of the present invention.

FIG. 8B is a diagram illustrating the intensity distribution of radially polarized light generated by a defect when a filter is disposed on the pupil plane in accordance with an embodiment of the present invention.

FIG. 11 is a block diagram illustrating a schematic configuration of a defect reviewing device according to an embodiment of the present invention.

FIG. 12A is a flowchart illustrating how the position of a defect is determined and reviewed by using the defect reviewing device according to an embodiment of the present invention.

FIG. 12B is a flowchart illustrating how the position of a defect is determined by using an optical microscope in accordance with an embodiment of the present invention.

FIG. 13 is a block diagram illustrating a schematic configuration of an optical microscope that uses a filter formed of a DMD in accordance with an embodiment of the present invention.

FIG. 14 is a block diagram illustrating a schematic configuration of an optical microscope that changes the polarization of a detected image by using a PBS in accordance with an embodiment of the present invention.

DESCRIPTION OF EMBODIMENTS

Figure 2:
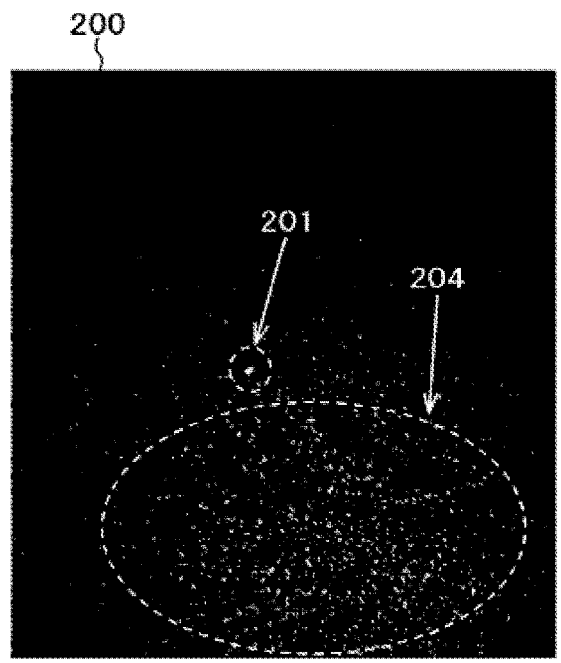
FIG. 2 is a dark-field image acquired in accordance with an embodiment of the present invention.

The present invention relates to a defect detection method and device that make it possible to detect microscopic defects with a dark-field optical microscope. The present invention also relates to a method and device for reviewing a defect detected by another inspection device by using the defect detection device.

Examples of the present invention will now be described with reference to the accompanying drawings.

EXAMPLE 1

First of all, an example of a defect reviewing device 100 that uses a dark-field optical microscope in accordance with the present invention will be described with reference to FIG. 1.

The defect reviewing device 100 according to the present example, which is illustrated in FIG. 1, includes an optical microscope 101, an image processing unit 120, a computation unit 130, an input/output unit 160, a storage unit 150, and a control unit 140. Although not shown in FIG. 1, the defect reviewing device 100 also includes an SEM that is used to review the details of a defect detected by the optical microscope 101. The control unit 140 is connected to an external data processing unit through a communication link (not shown).

The optical microscope 101, which acts as an imaging system, is configured appropriately by including an illumination unit 102 and an imaging optical system 114. The imaging optical system 114 operates so that a scattered light wafer image from a sample 103 is formed on an image pickup element 115. The image pickup element 115 is configured so that the polarization direction for transmission is set for each pixel. Thus, the image pickup element 115 is capable of simultaneously acquiring formed images having different polarization components. A distribution wavelength plate 109 is a wavelength plate having an optical axis that varies from one place to another. The distribution wavelength plate 109 is an optical element that converts each of different polarization directions of light to another direction on an individual place basis by using an optical axis set for each of various places. The image pickup element 115 and the distribution wavelength plate 109 will be described in detail later.

The imaging optical system 114 is configured appropriately by using an objective lens 106, an imaging lens 113, a spatial distribution optical element (filter) 112, a spatial distribution optical element switching mechanism 111, a height control mechanism 107, an element (distribution wavelength plate) 109, and the image pickup element 115. The spatial distribution optical element (filter) 112 and the spatial distribution optical element switching mechanism 111 are disposed on a pupil plane 110 between the objective lens 106 and the imaging lens 113. The height control mechanism 107 controls the height of the objective lens. The element (distribution wavelength plate) 109 is disposed on the pupil plane 110 to convert the polarization direction. The position of a pupil and its vicinity is referred to as the pupil plane 110.

The computation unit 130 includes a signal comparative computation unit 131 and a defect position calculation unit 132. The signal comparative computation unit 131 references data stored in the storage unit 150, compares the referenced data with the other stored data and data acquired from the optical microscope 101, and processes the data. The defect position calculation unit 132 calculates coordinates (defect position) of a captured and formed image by using the acquired data, the data stored in the storage unit, and the result of comparison made by the signal comparative computation unit 131.

The control unit 140 includes a filter control unit 141. The filter control unit 141 changes the type of the filter 112, moves the filter into and out of the pupil plane, and controls the transmission region of the filter. The filter 112 will be described in detail later. Processes performed in the signal comparative computation unit 131 and the defect position calculation unit 132 will be described in detail later.

An illumination optical system unit 102 is configured appropriately by using a light source 116 and a collecting lens 117. The collecting lens 117 collects light beams emitted from the light source 116 and sheds the collected light beams on a wafer 103.

The height control mechanism 107 may, for example, use a piezo element to move the objective lens, use a stepping motor and a ball screw to move the objective lens in Z direction along a linear guide (in a direction along the optical axis 108 of the imaging optical system 114), or use an ultrasonic motor and a ball screw to move the objective lens in Z direction along a linear guide.

In the present example, the filter 112 is an element that spatially shields a part of the pupil plane 110 from light. Multiple filters 112 having different properties (different light-shielding and transmission regions) are made available, and a filter holder 111 capable of switching from one filter to another is inserted into the pupil plane 110.

Further, the filter holder 111 can be driven (may be rendered rotatable about an axis parallel to the optical axis 108 although FIG. 1 indicates that the filter holder 111 is longitudinally driven in the direction of the arrow), and a filter 112 selected from among the multiple filters 112 retained on the pupil plane 110 by the filter holder 111 is installed over the optical axis 108. The filter holder 111 may retain only one filter (only one type of filter).

In order to prevent an image acquired by the image pickup element 115 from being disturbed when the filter 112 is not used, the position of the filter holder 111 is set for image observation so that the filter 112 is positioned outside the field of view of the objective lens 106. An alternative is to switch to a place where a parallel flat glass plate having the same thickness as the filter 112 is installed in the filter holder 111. The parallel flat glass plate having the same thickness as the filter 112 is installed in order to avoid a situation where an image of the wafer 103 is not formed on the image pickup element 115 when the filter 112 is removed to change the optical path length. Another alternative is to leave the parallel flat glass plate uninstalled and use a mechanism that forms an image on the image pickup element by adjusting the position of the imaging lens 113, which forms an image, or the position of the image pickup element 115.

Still another alternative is to use a DMD (digital mirror device) as the filter 112. The DMD is an optical element that is formed by disposing many small-size (micrometer-order size) light-reflecting mirrors on a plate. The direction of mirror reflection can be controlled for each mirror. When the direction of reflection is controlled to be on the optical axis, light at a particular place can be reflected toward the optical axis. Meanwhile, when the direction of reflection at a particular place is controlled to be outside the optical axis, light at the particular place is not reflected toward the optical axis and substantially blocked (controlling the direction of light reflection to be outside the optical axis is hereinafter referred to as light shielding or blocking). When the direction of mirror reflection at each position is controlled, control can be executed, for instance, to shield a light of only a particular place.

The optical microscope 101 shown in FIG. 1 is simplified for purposes of explanation. However, when the DMD is used as the filter 112, light cannot be transmitted because the DMD is an optical element that reflects light in a preselected part of the region or the whole region. When the DMD is used as the filter 112, therefore, an optical path needs to be configured as indicated for an optical microscope 1301 shown in FIG. 13.

The optical microscope 1301 shown in FIG. 13 includes an illumination unit 102, an objective lens 106, a distribution wavelength plate 109, a mirror 1311, an imaging lens 113, and a detector 115. The mirror 1311 reflects light toward the filter 112 formed of a DMD. The imaging lens 113 forms an image of light reflected from the filter 112 formed of the DMD. The filter 112 is disposed on the optical axis 1321 of light reflected from the mirror 1311, and the imaging lens 113 is disposed on the optical axis 1322 of light reflected from the filter 112 formed of the DMD. Thus, the DMD can be used as the filter 112. This enables the DMD to filter the pupil plane 110 in such a manner as to shield a part or the whole of the pupil plane 110 from light or leave the pupil plane 110 unshielded.

For the sake of explanation, even when the DMD is used, light reflected toward the optical axis 1322 is referred to as the transmitted light, a region reflected toward the optical axis 1322 is referred to as the transmission region, and a region not reflected toward the optical axis 1322 is referred to as the light-shielding region.

Further, when the filter 112 is formed of liquid crystal instead of a DMD so as to electrically change the transmission region of the filter 112, a configuration without the filter holder 111 can be formed. In this instance, individual liquid crystals forming the filter 112 can be driven to control whether or not to transmit light. Thus, the liquid crystals forming the filter 112 can be used to determine whether or not to filter the pupil plane 110.

When a DMD or liquid crystal is used as the filter 112 instead of using the filter holder 111, it is possible to reduce the time required for filter replacement, achieve an increased throughput, and avoid the aforementioned problem of a change in the optical path length by removing the filter 112.

In the present example, two pieces of the objective lens 106 and two pieces of the imaging lens 113 are used to form an image of the wafer 103 on the detection surface of the image pickup element 115. In the present example, multiple pieces of a lens may be disposed on the optical axis 108 in addition to the objective lens 106 and the imaging lens 113.

The optical microscope 101 is an imaging optical microscope having the imaging lens 113. A light-collecting optical microscope without the imaging lens 113 can detect whether a defect exists in a region where scattered light captured by the objective lens 106 is generated (in the field of view of the optical microscope), but cannot determine the position of a defect in the region (in the field of view of the optical microscope). Meanwhile, the imaging optical microscope 101 forms an image with the imaging lens 113 and acquires the formed image. This makes it possible to acquire information that is obtained when a region where scattered light captured by the objective lens 106 is generated is divided into pixels within the image. When the region where the scattered light is generated is divided into pixels within the formed image to determine the position of a defect in the formed image, the detailed position of the defect in the region where the scattered light is generated can be identified to improve the accuracy of position detection. The imaging optical microscope 101 achieves position detection with high accuracy. Therefore, when an SEM having a higher magnification than the optical microscope 101 is used to capture an image of a position at which a defect detected by the optical microscope 101, the image can be captured in such a manner that the defect is positioned within the FOV of the SEM.

Roughness scattered light in a dark-field image, which obstructs the detection of a defect, will now be described with reference to FIG. 2. A dark-field image 200 is obtained by forming an image of defect scattered light that is tens of nanometers in size. A bright spot 201 in the dark-field image 200 is a scattered light image of a defect. The other bright spots, such as bright spots existing in a region enclosed by a broken-line oval 204, form a scattered light image derived from roughness. The scattered light image derived from a defect is an image of an electromagnetic wave that is generated when the defect is excited and polarized by illumination light (electromagnetic wave). The defect scattered light is generated only from the defect. Meanwhile, the scattered light image derived from roughness is a speckle pattern image generated due to the interference of scattered light that is generated by the polarization of surface irregularities of several angstroms in size in the whole irradiation region of illumination.

The brightness of a defect scattered light image and the brightness of a roughness scattered light image, which are included in the formed image, are related to the respective scattered light intensity. In general, the higher the scattered light intensity, the higher the brightness in a formed image.

Defect scattered light and roughness scattered light differ in the polarization intensity distribution of scattered light. The example of FIG. 2 shows a dark-field image based on one polarization direction. However, the present invention acquires a dark-field image based on each polarization direction and compares the brightness values of individual polarization directions of each pixel in the image in order to distinguish between a scattered light image derived from a defect and a scattered light image derived from roughness.

Scattered light intensity difference between roughness scattered light and defect scattered light, which depends on the polarization direction, will now be described with reference to FIGS. 3A to 3D. The polarization direction varies, for example, with the configuration of an optical system. For the sake of explanation, various polarization directions are defined below.

A polarization direction oscillating in radial direction with respect to the optical axis on the pupil plane 110 is referred to as the direction of radial polarization. A polarization direction oscillating in parallel with a plane that is orthogonal to radially polarized light and perpendicular to the optical axis (the polarization direction oscillating in concentric direction) is referred to as the direction of azimuth polarization.

When the polarization direction is uniform in the pupil plane 110, the X direction is parallel to a plane orthogonal to the optical axis and parallel to an illumination incidence direction, and the Y direction is perpendicular to the illumination incidence direction, linearly polarized light that is parallel to the plane orthogonal to the optical axis and oriented in X direction on the pupil plane is referred to as P-polarized light, and linearly polarized light that is parallel to the plane orthogonal to the optical axis and oriented in a direction orthogonal to P-polarized light (oriented in Y direction) is referred to as S-polarized light.

The examples of FIGS. 3A to 3D illustrate the radially or azimuthally polarized light intensity distribution on the pupil plane 110 of scattered light from minute irregularities of a substrate surface (roughness scattered light) and scattered light from minute foreign matter in accordance with calculations based on scattered light simulation.

Figure 3A:
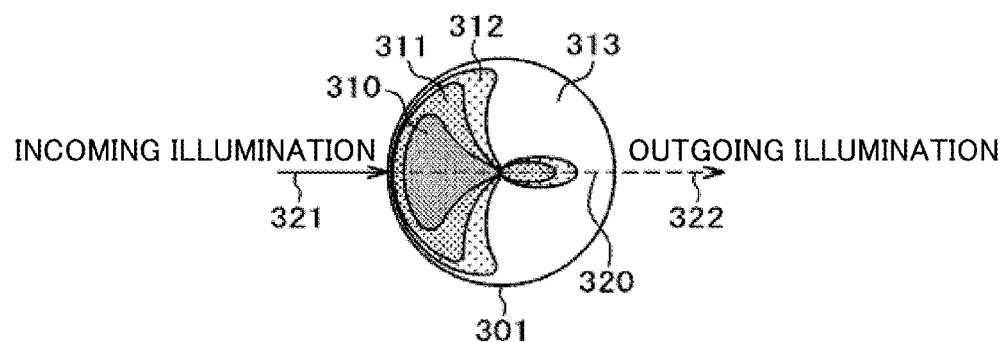
FIG. 3A is a diagram illustrating the radially polarized light intensity distribution of roughness scattered light on a pupil plane.
Figure 3B:
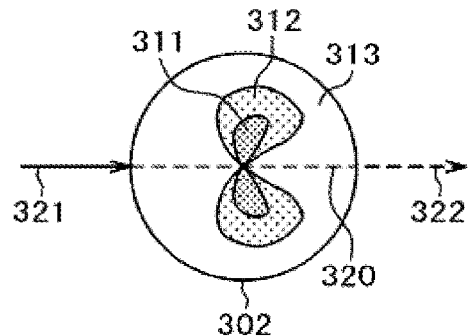
FIG. 3B is a diagram illustrating the azimuthally polarized light intensity distribution of roughness scattered light on a pupil plane.
Figure 3C:
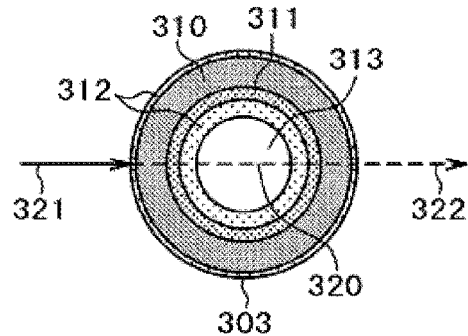
FIG. 3C is a diagram illustrating the radially polarized light intensity distribution of scattered light from minute foreign matter on a pupil plane.

FIG. 3A illustrates the radially polarized light intensity distribution of roughness scattered light 301. FIG. 3B illustrates the azimuthally polarized light intensity distribution of roughness scattered light 302. FIG. 3C illustrates the radially polarized light intensity distribution of scattered light from minute foreign matter (spherical foreign matter) 303. FIG. 3D illustrates the azimuthally polarized light intensity distribution of scattered light from minute foreign matter 304.

A region 310 in FIGS. 3A to 3D has a high scattered light intensity, a region 311 has a relatively high scattered light intensity, a region 312 has a relatively low scattered light intensity, and a region 313 has a low scattered light intensity. An axis 320 is an axis along which the incident light axis of illumination correlates with the pupil plane 110.

As is obvious from FIGS. 3A and 3C, the radially polarized light intensity of scattered light from roughness is high on the side toward an illumination incidence side 321 (backscattering) and high in a part of a region toward an illumination incidence side 322 (forward-scattering), but the intensity of scattered light from minute foreign matter is substantially isotropically high in a large region on the circumference of the pupil plane 110. Meanwhile, FIGS. 3B and 3D indicate that the azimuthally polarized light intensity of scattered light from roughness is relatively high in a region near the center of the pupil plane 110, but that the intensity of scattered light from minute foreign matter is low in the whole region.

The intensity distribution on the pupil plane 110 of scattered light from roughness only or from minute foreign matter only has been described. In reality, however, scattered light from roughness and scattered light from minute foreign matter coexist on the pupil plane 110. Additionally, the dark-field image 200 that can be captured by the detector 115 is not a scattered light intensity distribution image of the pupil plane 110, but is an image of the pupil plane 1110 that is formed by the imaging lens. Therefore, an actual captured image is an image of the pupil plane that is formed by the imaging lens while the pupil plane shows scattered light intensity distribution in which scattered light from roughness and scattered light from minute foreign matter are mixed.

As the scattered light distribution on the pupil plane 110 of roughness differs in properties from the scattered light distribution on the pupil plane 110 of minute foreign matter, the scattered light from minute foreign matter can be distinguished from the scattered light from roughness. The imaging position of the scattered light from minute foreign matter, that is, the position of the scattered light on the image pickup element 115, can then be detected to determine the coordinates indicative of a candidate defect position (defect candidate).

Further, the present invention examines a defect candidate by making use of the difference in the polarization intensity distribution on the pupil plane 110 between the scattered light from roughness and the scattered light from minute foreign matter, which is indicated in FIGS. 3A to 3D, and excludes a roughness region that cannot be identified simply by comparing the brightness values of a radially polarized light dark-field image and an azimuthally polarized light dark-field image. When the filter 112 shielding light from the regions 310, 311, 312 where the roughness scattered light intensity of radially polarized light is high as indicated in FIG. 3A is disposed on the pupil plane 110, the radially polarized light intensity of roughness scattered light greatly decreases due to the difference in intensity distribution. However, as indicated in FIG. 3C, the decrease in the radially polarized light intensity of scattered light from minute foreign matter having a high intensity substantially uniformly in a large region on the circumference is not as great as the decrease in the radially polarized light intensity of roughness scattered light. This property is used to let the signal comparative computation unit 131 compare the radially polarized light intensity of a defect candidate that is obtained while the filter is not disposed with the radially polarized light intensity of the defect candidate that is obtained while the filter is disposed, extract a defect candidate that exhibits a small decrease in scattered light intensity, and allow the defect position calculation unit 132 to calculate the position of the extracted defect candidate.

The difference between the intensity distribution on the pupil plane 110 of scattered light from minute foreign matter, which is an example of a defect, and the intensity distribution of roughness scattered light has been described. However, a different type of defect (such as a scratch) exhibits a different scattered light intensity distribution on the pupil plane 110. In such an instance, the filter 112 should be changed to a filter having a different transmission region that matches the scattered light distribution properties of a target defect. The filter 112 may be changed by using the filter holder 111. An alternative is to change the transmission region by using, for example, a DMD or liquid crystal.

Figure 4B:
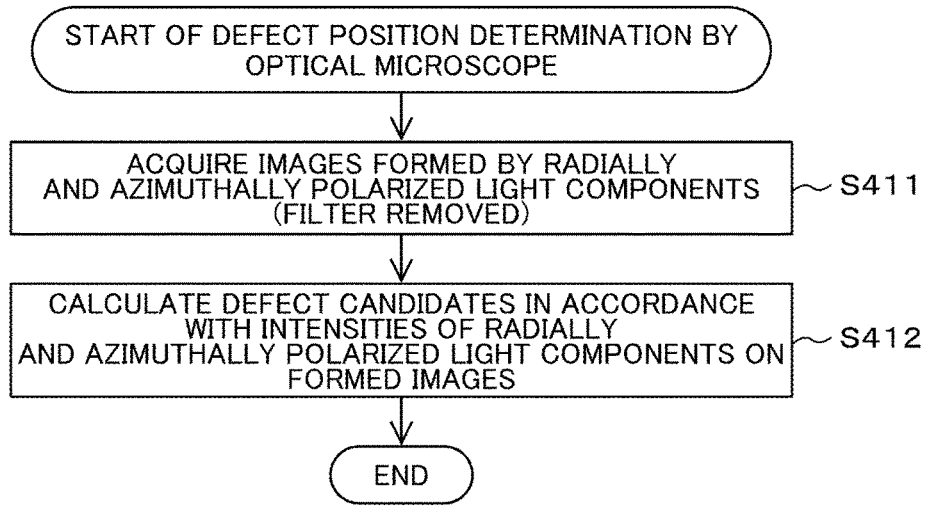
FIG. 4B is a flowchart illustrating how the position of a defect is determined based on the intensities of a radially polarized light component and azimuthally polarized light component when an optical inspection device according to an embodiment of the present invention is used for defect position determination.

Defect imaging steps according to the present invention will now be described with reference to FIGS. 4A to 4D. FIG. 4A is an exemplary flowchart illustrating in which a defect position on a wafer is identified with an optical microscope and an image of the position identified defect is captured with an SEM.

First of all, based on defect position information obtained by inspecting a wafer 103 with another defect inspection device, a stage 104 is moved so that the wafer 103 is illuminated with light from the illumination unit 102 of the optical microscope 101 (step S401).

Next, an image of a defect on the wafer 103 is captured by the optical microscope 101 and the position of the defect is identified by the computation unit 130 (step S402). The stage 104 is then moved to a sample review position of the SEM to allow the SEM to capture an image of the defect whose position is identified in step S402 (step S403).

Figure 4C:
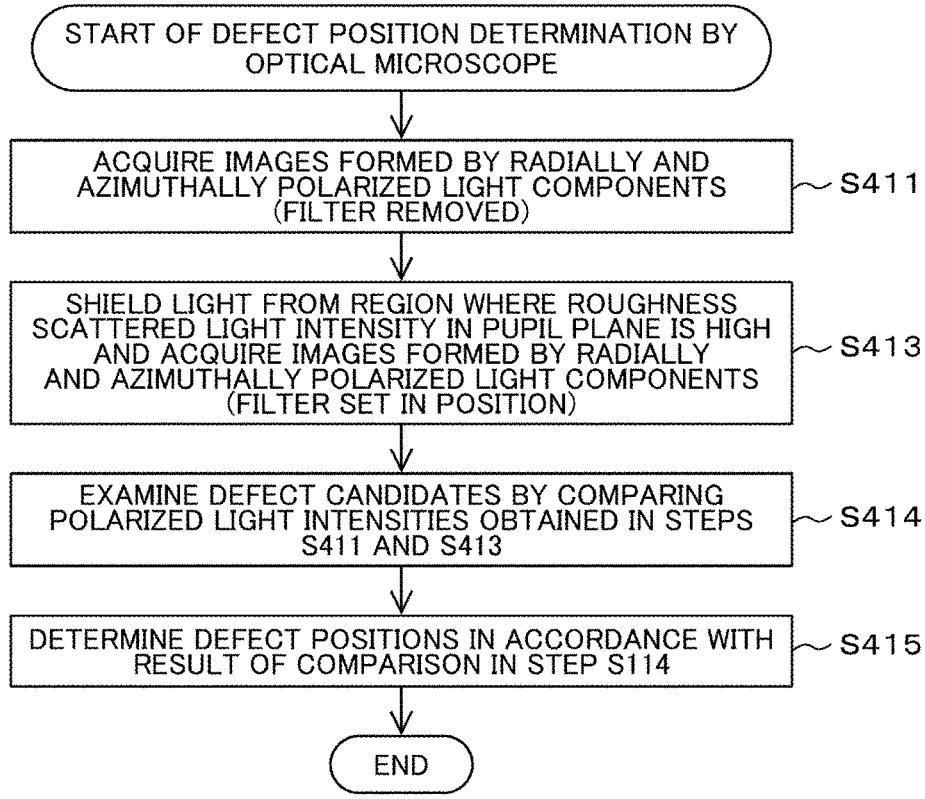
FIG. 4C is a flowchart illustrating how the position of a defect is determined by using an image obtained from filtering and an image obtained without filtering when the optical inspection device according to an embodiment of the present invention is used for defect position determination.
Figure 4D:
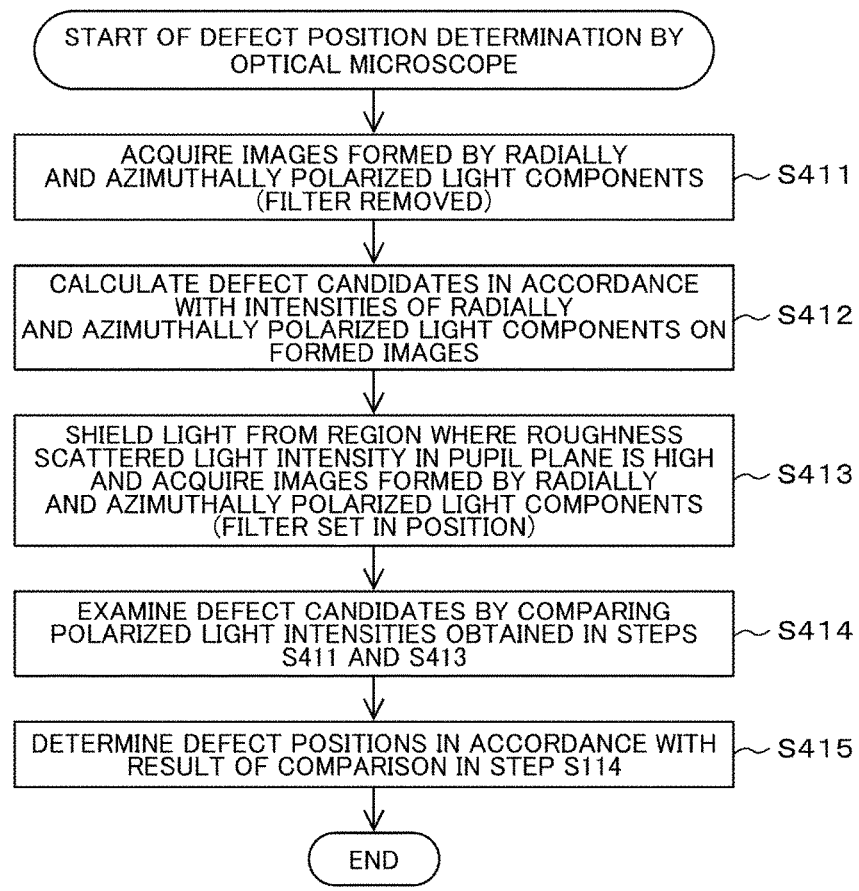
FIG. 4D is a flowchart illustrating how the position of a defect is determined by using the intensities of the radially polarized light component and azimuthally polarized light component, an image obtained from filtering, and an image obtained without filtering when the optical inspection device according to an embodiment of the present invention is used for defect position determination.

FIGS. 4B to 4D are detailed flowcharts illustrating a defect position identification process (step S402) performed by the optical microscope according to the present invention. A method of extracting a defect candidate in accordance with the intensity of a polarization component will now be described with reference to FIG. 4B.

First of all, formed images of radially and azimuthally polarized light components are acquired while no filtering is performed by the filter 112 on the pupil plane 110 (step S411). The filter 112 can be prevented from performing filtering by removing the filter 112 by using the filter holder 111 or by dynamically changing the transmission region of the filter by using, for example, a DMD or liquid crystal. The method of separately acquiring the formed images of radially and azimuthally polarized light components will be described in detail later.

Next, the signal comparative computation unit 131 examines the formed images of radially and azimuthally polarized light components, which are captured in step S411, compares the brightness values of pixels at the same or nearby position, and allows a defect position identification unit 132 to calculate a defect candidate (step S412). The method of calculating a defect candidate will be described in detail later.

A method of extracting a defect candidate by using an image captured, depending on whether the filter is present, will now be described with reference to FIG. 4C. First of all, as is the case with step S411 in FIG. 4B, the formed images of radially and azimuthally polarized light components are acquired while no filtering is performed by the filter 112 on the pupil plane 110 (step S411). The formed images of radially and azimuthally polarized light components are then acquired while filtering is performed by the filter 112 shielding light from a region where the roughness scattered light intensity in the pupil plane is high (step S413). Next, the signal comparative computation unit 131 compares the intensity of radially/azimuthally polarized light that is obtained when no filtering is performed in step S411 with the intensity of radially/azimuthally polarized light that is obtained when filtering is performed in step S413 (step S414).

Finally, based on the comparison made in step S414, the defect position identification unit 132 determines the position of a defect (step S415). The method of identifying a position of a defect in steps S414 and S415 will be described later.

A method of identifying a position of a defect, which is obtained by integrating the method described with reference to FIG. 4B with the method described with reference to FIG. 4C, will now be described with reference to FIG. 4D.

First of all, the formed images of radially and azimuthally polarized light components are acquired while no filtering is performed by the filter 112 on the pupil plane 110 (step S411). The filter 112 can be prevented from performing filtering by removing the filter 112 by using the filter holder 111 or by dynamically changing the transmission region of the filter by using, for example, a DMD or liquid crystal.

Next, the signal comparative computation unit 131 examines the formed images of radially and azimuthally polarized light components, which are captured in step S411, compares the brightness values of pixels at the same or nearby position, and allows the defect position identification unit 132 to calculate a defect candidate (step S412). Subsequently, the formed images of radially and azimuthally polarized light components are acquired while filtering is performed by the filter 112 shielding light from a region where the roughness scattered light intensity in the pupil plane is high (step S413).

Next, the signal comparative computation unit 131 compares radially and azimuthally polarized light intensities of the defect candidate calculated in step S412 that are acquired in steps S411 and S413 when no filtering is performed and filtering is performed (step S414). Finally, based on the comparison made in step S414, the defect position identification unit 132 identifies a position of a defect (step S415). The method of identifying a position of a defect in steps S414 and S415 will be described later.

The flowcharts of FIGS. 4B to 4D describe an example in which minute foreign matter is to be distinguished from roughness. Therefore, the method of capturing the formed images of azimuthally and radially polarized light components and comparing obtained signals is described with reference to the flowcharts. However, the direction of polarization to be imaged is not limited to the combination of radial and azimuth polarization directions.

In order to accurately determine the position of a defect in accordance with the flowcharts of FIGS. 4B to 4D, it is necessary to examine the formed images of radially and azimuthally polarized light components by comparing the brightness values of pixels at the same or nearby position. For such a comparison, it is essential that the correspondence between pixels at the same or nearby position be guaranteed for the images formed in the individual polarization directions (that is, the spatial correspondence needs to be guaranteed for the images formed in the individual polarization directions).

A method of separately capturing, in steps S411 and S413, the formed images of radially and azimuthally polarized light components for which the spatial correspondence is guaranteed will now be described with reference to FIGS. 5A to 5C and FIGS. 6A to 6C.

In order to separately acquire the formed images of radially and azimuthally polarized light components, it is necessary to separate radially polarized light from azimuthally polarized light and capture their images separately with a detector on the imaging plane. The present example converts the polarization directions to P-polarization and S-polarization with the distribution wavelength plate 109 on the pupil plane and disposes a polarization filter transmitting P-polarized light only or S-polarized light only in front of elements corresponding to the pixels of the detector 115 to separately acquire the images of P- and S-polarized light components.

The distribution wavelength plate 109 is such that an optical axis is set at each of various positions on the distribution wavelength plate, and is capable of converting a polarization direction under conditions predefined for each of the various positions. The distribution wavelength plate 109 can be implemented, for instance, by combining photonic crystal with a ½ wavelength plate or a ¼ wavelength plate.

The distribution wavelength plate 109, which converts radially and azimuthally polarized light components to P-polarized light and S-polarized light, will now be described with reference to FIGS. 5A to 5C.

Figure 5A:
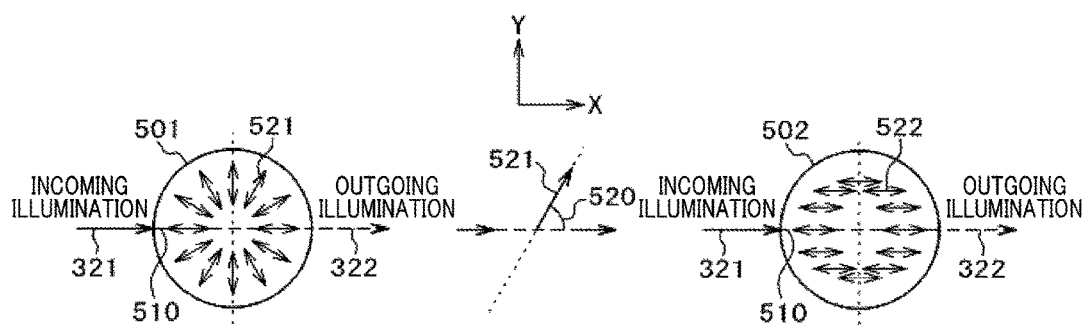
FIG. 5A is a diagram illustrating an example in which radially polarized light is converted to P-polarized light on a pupil plane by using a distribution wavelength plate in accordance with an embodiment of the present invention.

FIG. 5A illustrates an example in which radially polarized light 521 on the pupil plane 110 is converted to P-polarized light 522 by using the distribution wavelength plate 109. The reference numeral 501 denotes a state of radial polarization of scattered light in the vicinity of the pupil plane 110 before transmission through the distribution wavelength plate 109. The reference numeral 502 denotes a state of polarization of scattered light in the vicinity of the pupil plane 110 after transmission through the distribution wavelength plate 109. When a ½ wavelength plate 532 whose relationship to a phase lag axis and a phase advance axis is indicated at 530 as indicated in FIG. 5B and whose phase advance axis is tilted at an angle 531, which is half an angle 520, with respect to the X-axis (P-polarization direction axis) direction 510, is disposed on the pupil plane 110 with respect to a polarization direction 521 tilted at an angle 520 with respect to the X-axis (P-polarization direction axis) direction 510, the polarization direction 521 tilted at the angle 520 with respect to the X-axis (P-polarization direction axis) direction 510 is converted to a polarization direction 522 parallel to the X-axis direction 510 (that is, P-polarization). Radially polarized light can be converted to P-polarized light by disposing, on the pupil plane 110, the distribution wavelength plate 109 having an optical axis distribution for converting radially polarized light to P-polarized light in accordance with an in-plane identifying the position.

FIG. 5C illustrates an example in which azimuthally polarized light on the pupil plane 110 is converted to S-polarized light by using the distribution wavelength plate 109.

The reference numeral 503 denotes a state of azimuth polarization 5031 of scattered light in the vicinity of the pupil plane 110 before transmission through the distribution wavelength plate 109. The reference numeral 502 denotes a state of S-polarization 5041 of scattered light in the vicinity of the pupil plane 110 after transmission through the distribution wavelength plate 109. The polarization direction of azimuthally polarized light 5031 indicated at 503 is perpendicular to the polarization direction of radially polarized light 521. Therefore, using the distribution wavelength plate 109 that converts radially polarized light to P-polarized light makes it possible to convert azimuthally polarized light 5031 to the polarization direction of S-polarized light 5041 (direction perpendicular to the direction of P-polarized light). Disposing the above-described distribution wavelength plate 109 on the pupil plane 110 provides an advantage because it makes it possible to simultaneously convert radially polarized light to P-polarized light and azimuthally polarized light to S-polarized light. An alternative is to use the distribution wavelength plate 109 that is characterized to similarly convert radially polarized light to S-polarized light and azimuthally polarized light to P-polarized light.

The detector 115 for capturing images of radially polarized light and azimuthally polarized light, which are converted to P-polarized light and S-polarized light by using the distribution wavelength plate 109, as separate images whose spatial correspondence on a single imaging plane is guaranteed will now be described with reference to FIG. 6A.

Figure 6A:
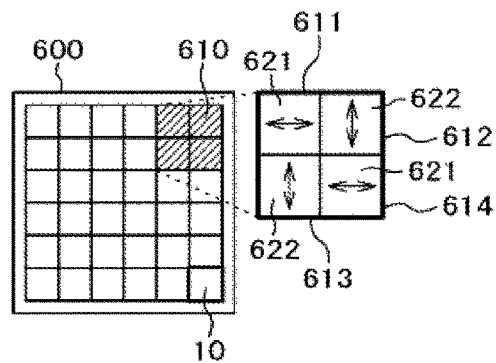
FIG. 6A is a plan view of a detector that captures images of radially polarized light and azimuthally polarized light, which are converted to P-polarized light and S-polarized light by a distribution wavelength plate in accordance with an embodiment of the present invention, as separate images formed on a single imaging plane with spatial relationship guaranteed. This plan view illustrates the detector that separately captures the images formed in different polarization directions.
Figure 6B:
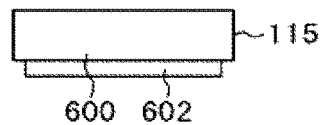
FIG. 6B is a plan view of a detector that captures images of radially polarized light and azimuthally polarized light, which are converted to P-polarized light and S-polarized light by a distribution wavelength plate in accordance with an embodiment of the present invention, as separate images formed on a single imaging plane with spatial relationship guaranteed.

As indicated in FIGS. 6A and 6B, using the detector having a polarization filter 602 that transmits P-polarized light and S-polarized light and is disposed in front of a region corresponding to each pixel 601 on a light-receiving plane 600 makes it possible to detect the formed images of P- and S-polarized light components by using different pixels and separately capture the formed images. The reference numeral 610 denotes a set of four neighboring pixels 611 to 614 in the light-receiving plane. A polarization filter 621, which transmits P-polarized light only, is disposed in front of the pixels 611 and 614. A polarization filter 622, which transmits S-polarized light only, is disposed in front of the pixels 612 and 613.

When the set of four neighboring pixels 610 is used as one set (one unit of pixels), the scattered light intensities of P-polarized light and S-polarized light at substantially the same position on the wafer 103 can be acquired (that is, the scattered light intensities of individual polarization directions whose spatial correspondence is guaranteed can be acquired). In this instance, polarization filters allowing neighboring pixels to transmit variously oriented polarizations may be disposed, or polarization filters in one set may be disposed arbitrarily.

Figure 6C:
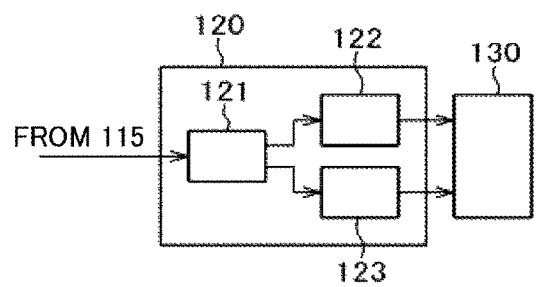
FIG. 6C is a block diagram illustrating a configuration of an image processing unit that separately processes a P-polarized image and S-polarized image detected by a detector.
Figure 7C:
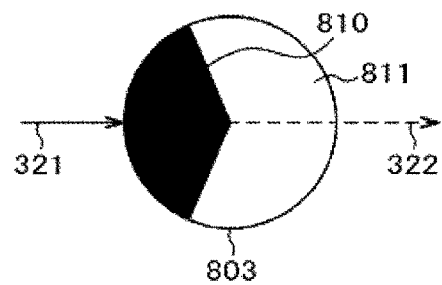
FIG. 7C is a diagram illustrating an exemplary shape of the filter disposed on the pupil plane in accordance with an embodiment of the present invention.
Figure 7D:
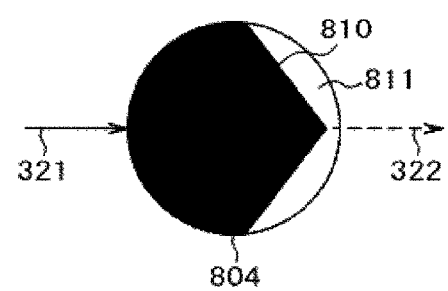
FIG. 7D is a diagram illustrating an exemplary shape of the filter disposed on the pupil plane in accordance with an embodiment of the present invention.
Figure 7E:
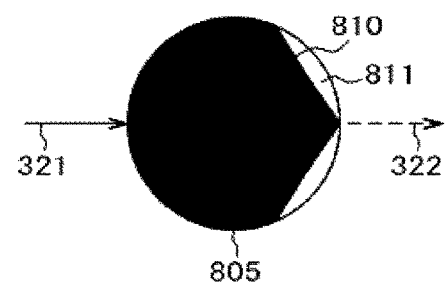
FIG. 7E is a diagram illustrating an exemplary shape of the filter disposed on the pupil plane in accordance with an embodiment of the present invention.

In order to separately capture the formed images of P-polarized light and S-polarized light, for example, the image processing unit 120 shown in FIG. 1 preferably includes an input unit 121, a P-polarized image processing unit 122, and an S-polarized image processing unit 123, as indicated in FIG. 6C. In the image processing unit 120, the input unit 121 receives a signal outputted from the detector 115, and the received signal is branched so that output signals from the pixels 611 and 614, which are included in one set of pixels (one unit of pixels) of the detector 115 and have detected P-polarized light, are outputted to the P-polarized image processing unit 122, and that output signals from the pixels 612 and 613 are inputted to the S-polarized image processing unit 123.

In the P-polarized image processing unit 122, the average brightness value of the output signals from the pixels 611 and 614 is used as the brightness value of P-polarized light in pixels at the same position (that is, used as the brightness value of individual polarization directions whose spatial correspondence is guaranteed). In the S-polarized image processing unit 123, the average brightness value of the output signals from the pixels 612 and 613 is used as the brightness value of S-polarized light in pixels at the same position (that is, used as the brightness value of individual polarization directions whose spatial correspondence is guaranteed). Images are then separately generated by using the brightness values of the individual polarization directions. In this instance, when the brightness values of the individual polarization directions whose spatial correspondence is guaranteed are used as the brightness values at the same coordinates of the images formed in the individual polarization directions, the spatial correspondence between the pixels in the images formed in the individual polarization directions can be guaranteed.

Image data processed by the P-polarized image processing unit 122 and image data processed by the S-polarized image processing unit 123 are outputted to the computation unit 130. As P-polarized light and S-polarized light are obtained by converting the radially and azimuthally polarized light directions, they can be handled as images identical with the formed images of radially and azimuthally polarized light components.

Although the above example relates to a case where one set (one unit of pixels) is formed of four pixels, the above-described method is also applicable to a case where the number of pixels is other than four. Further, the arrangement of pixels 611 and 612 in the set 610 is merely an example. The above-described method is applicable to any arrangement in which the pixels 611 and 612 are close to each other.

The brightness value of P-polarized light that is acquired by the pixels 611 and 614 for which a filter transmitting nearby P-polarized light only is disposed may be used to estimate the brightness value of S-polarized light that is acquired by the pixels 612 and 613 for which a filter transmitting nearby S-polarized light only is disposed. Estimation may be achieved by linear interpolation or by interpolation based on curve fitting. In a similar manner, the brightness value of S-polarized light that is acquired by the pixels 612 and 613 for which the filter transmitting nearby S-polarized light only is disposed may be used to estimate the brightness value of P-polarized light. When images are derived from the brightness values of P-polarized light and S-polarized light, which are estimated by the pixels, the formed images of P-polarized light and S-polarized light can be separately captured. This method makes it possible to acquire the scattered light intensities of P-polarized light and S-polarized light from all pixels in the light-receiving plane of the detector, and is advantageous in that resolution does not deteriorate.

Figure 15A:
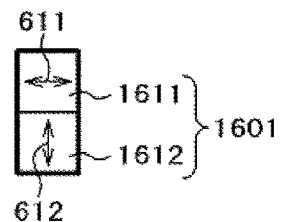
FIG. 15A is a partial plan view of a detector having a pixel combination in which a pixel detecting a P-polarized image and a pixel detecting an S-polarized image are arranged in vertical direction to form one set of pixels in accordance with an embodiment of the present invention.
Figure 15B:
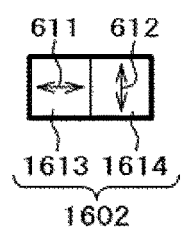
FIG. 15B is a partial plan view of a detector having a pixel combination in which a pixel detecting a P-polarized image and a pixel detecting an S-polarized image are arranged in horizontal direction to form one set of pixels in accordance with an embodiment of the present invention.

A case where the number of pixels included in one set (one unit of pixels) is other than four will now be described with reference to FIGS. 15A to 15C. FIGS. 15A and 15B illustrate examples in which one set (one unit of pixels) is formed of two pixels. The formed images of P-polarized light and S-polarized light can be separately captured by using a pixel 1611 for which a P-polarization filter 611 in one set (1601 or 1602) is disposed and a pixel for which an S-polarization filter 612 is disposed, for the brightness values of P-polarized light and S-polarized light at pixels at the same positions, and allowing the P-polarized image processing unit 122 and the S-polarized image processing unit 123 to separately generate images by using the brightness values obtained in the respective polarization directions.

Figure 15C:
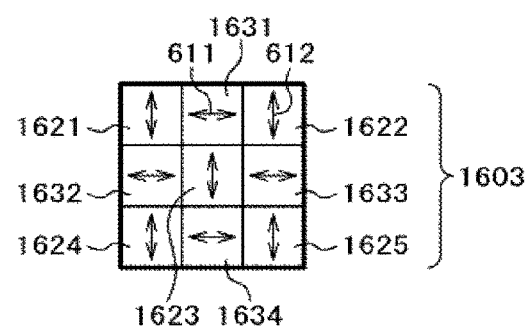
FIG. 15C is a partial plan view of a detector having a pixel combination in which a pixel detecting a P-polarized image and a pixel detecting an S-polarized image are alternately arranged in vertical direction and horizontal direction to form one set of nine pixels in accordance with an embodiment of the present invention.

FIG. 15C illustrates an example in which one set (one unit of pixels) of the light-receiving plane 600 is formed of nine pixels. Referring to FIG. 15C, the formed images of P-polarized light and S-polarized light can be separately captured, for example, by using the average brightness values obtained in the individual polarization directions, which are derived from pixels 1631 to 1634 for which the P-polarization filter 611 in one set is disposed and pixels 1621 to 1625 for which the S-polarization filter 612 is disposed, as the brightness values of P-polarized light and S-polarized light at pixels at the same positions, and allowing the P-polarized image processing unit 122 and the S-polarized image processing unit 123 to separately generate images by using the brightness values obtained in the respective polarization directions. An alternative method is to use the maximum brightness values obtained in the individual polarization directions, which are derived from the pixels 1631 to 1634 for which the P-polarization filter 611 in the same set is disposed and the pixels 1621 to 1625 for which the S-polarization filter 612 is disposed, as the brightness values of P-polarized light and S-polarized light at pixels at the same positions. Another alternative method is to use the intermediate brightness values obtained in the individual polarization directions as the brightness values of P-polarized light and S-polarized light at pixels at the same positions.

The number of pixels included in one set of the light-receiving plane 600 is not limited to those described with reference to FIG. 6A and FIGS. 15A to 15C. The above-described methods are applicable as far as two or more pixels are included in one set of the light-receiving plane 600, and the spatial correspondence between the pixels can be guaranteed, as is the case with the examples of FIG. 6A and FIGS. 15A to 15C.

The above examples are used to describe a case where radially polarized light and azimuthally polarized light are converted to P-polarized light and S-polarized light by using the distribution wavelength plate 109, and the formed images of P-polarized light and S-polarized light are separately captured by using the detector 115 configured so that a filter transmitting P-polarized light only or a filter transmitting S-polarized light only is disposed for individual pixels.

The direction of polarization transmitted through filters 602 disposed in front of the pixels on the light-receiving plane 600 of the detector 115 is rendered identical with the polarization direction derived from conversion performed by the distribution wavelength plate 109 in order to let the detector 115 acquire the images formed in the radial and azimuth polarization directions. In this manner, the formed images of the polarization components can be captured with high sensitivity. Let us assume that the transmission directions of the polarization filters 602 disposed in front of the light-receiving plane 600 of the detector 115 are direction 1 and direction 2, and that direction 1 and direction 2 are parallel to a plane orthogonal to the optical axis and are orthogonal to each other. If the distribution wavelength plate 109 is formed of a combination of ½ wavelength plates, the optical axis should be set so that the angle 531 between direction 1 and the phase advance axis indicated in FIG. 5B is half the angle between direction 1 and the radial polarization direction 521 indicated in FIG. 5A. The polarization direction of azimuthally polarized light is orthogonal to the polarization direction of radially polarized light, and direction 2 is orthogonal to direction 1. Thus, the direction of azimuth polarization can be converted to direction 2 by using the distribution wavelength plate 109 having an optical axis distribution that converts the direction of the above-mentioned radial polarization to direction 1.

The above-described process of separately acquiring the formed images of radially and azimuthally polarized light components is summarized below. First of all, the illumination unit 102 illuminates the wafer 103 with illumination light, and the objective lens 106 captures the scattered light from the wafer 103. Next, the distribution wavelength plate 109 disposed on the pupil plane 110 converts radially polarized light and azimuthally polarized light transmitted through the pupil plane to P-polarized light and S-polarized light by the method described with reference to FIGS. 5A to 5C.

When the pupil plane 110 is to be filtered with the filter 112 (step S413), the filter holder 111 is used to insert the filter 112 into its position on the pupil plane 110. An alternative is to perform filtering, for example, by setting a non-transmission region on the pupil plane 110 through the use of a DMD or liquid crystal. Filtering of the pupil plane 110 will be described in detail later. When no filtering is to be performed (step S411), the filter holder 111 is used to remove the filter 112 from the pupil plane. An alternative is to set the whole region on the pupil plane 110 as a transmission region by using, for example, a DMD or liquid crystal.

The imaging lens 113 is used to form an image of scattered light on the detector 115, and the method described with reference to FIGS. 6A to 6C is used to let each pixel 601 of the detector 115 detect P-polarized light or S-polarized light. In this manner, the images of radially and azimuthally polarized light components are acquired.

A device that is not configured to use the detector 115 described with reference to FIGS. 6A to 6C and is adapted to separately acquire the formed images of radially and azimuthally polarized light components in such a manner as to guarantee the spatial correspondence will now be described with reference to FIG. 14. FIG. 14 illustrates a configuration of an optical microscope 1501 that is capable of separately capturing the formed images of radially polarized light and azimuthally polarized light. The optical microscope 1501 differs in configuration from the optical microscope 101 described with reference to FIG. 1. More specifically, the optical microscope 1501 uses a detector 1512 instead of the detector 115 and additionally includes a polarization beam splitter (PBS) 1511. Elements identical with the corresponding elements of the optical microscope 101 described with reference to FIG. 1 are designated by the same reference numerals as those of the corresponding elements and will not be redundantly described.

The PBS 1511 separates the optical axes of P-polarization and S-polarization, transmits either P-polarized light or S-polarized light, and blocks the remaining polarized light. The PBS 1511 is capable of changing the polarization direction for transmission by rotating it 90 degrees in the direction of rotation 1521 around the optical axis 108.

A control unit 145 includes a PBS control unit 1512 in addition to the elements of the control unit 140 described with reference to FIG. 1. The PBS control unit 1512 changes the polarization direction for the transmission from the PBS 1511. The detector 1512 is connected to the image processing unit 120, the computation unit 130, the control unit 140, the storage unit 150, and the input/output unit 160. The PBS 1511 is connected to the PBS control unit 1542.

Scattered light is generated on the surface of the wafer 103 that is illuminated with illumination light emitted from the illumination unit 102. The scattered light is then partly incident on the objective lens 106 and collected. Next, the collected scattered light is passed through the distribution wavelength plate 109 and separated into P-polarized light and S-polarized light. The scattered light, which is separated into P-polarized light and S-polarized light, is then incident on the PBS 1511, which is installed over the optical axis 108.

In this instance, the PBS 1511 is controlled and set by the PBS control unit 1542 so as to transmit the P-polarized light without transmitting the S-polarized light. Only the scattered light of P-polarized light is transmitted through the PBS 1511 so that the imaging lens 113 forms an image of the P-polarized light on the light-receiving plane of the detector 1512. Thus, the detector 1512 captures the formed image of a P-polarized light component of the scattered light.

Subsequently, the PBS control unit 1542 controls the PBS 1511 so that the PBS 1511 transmits S-polarized light and does not transmit P-polarized light. The imaging lens 113 then forms an image of the S-polarized light transmitted through the PBS 1511. Thus, the detector 1512 captures the formed image of an S-polarized light component of the scattered light.

Even when the PBS 1511 rotates in the rotation direction 1521 around the optical axis 108, the optical axis for light transmitted through the PBS 1511 does not change. Therefore, the spatial correspondence between the images formed in the individual polarization directions is guaranteed.

Using the optical microscope 1501 is advantageous in that the resolution of an image formed in each polarization direction does not deteriorate.

The methods of separately capturing the formed images of two different polarized light components, that is, radially and azimuthally polarized light components, with the spatial correspondence guaranteed has been described with reference to FIGS. 5A to 5C and FIGS. 6A to 6C. However, the method is applicable not only to radially and azimuthally polarized light components, but also to the other polarized light components. Further, the method described with reference to FIGS. 6A to 6C can also be applied to a case where a combination of three or more different polarization directions is targeted for acquisition.

The filter 112 will now be described with reference to FIGS. 7A to 7E and FIGS. 8A and 8B. As described with reference to FIGS. 3A to 3D, the intensity distribution of scattered light on the pupil plane 110 varies with the type of defect and with the direction of polarization. In order to distinguish between defect scattered light and roughness scattered light, the present example is configured so that the filter 112 is disposed on the pupil plane 110 to increase the intensity difference between filtered defect scattered light and filtered roughness scattered light. When minute defect scattered light is to be distinguished from roughness scattered light, the difference in scattered light intensity on an imaging plane is increased by performing filtering with a filter that is disposed on the pupil plane 110 to shield light from a region where the roughness scattered light intensity of radially scattered light is high.

FIGS. 7A to 7E illustrate filters 801 to 805 as the examples of the filter 112 that distinguishes between minute defect scattered light and roughness scattered light of radially polarized light. The filter 112 is disposed on the pupil plane 110 to shield a region 810 on the pupil plane 110 from light and transmit light through a region 811. As explained with reference to FIGS. 3A to 3D, the result of simulation indicates that the roughness scattered light of radially polarized light exhibits a high intensity distribution on the illumination incidence side on the pupil plane 110. Therefore, shielding such a region from light increases the intensity difference of the roughness scattered light from defect scattered light on the imaging plane. The filters 801 to 805 satisfy the above-described conditions.

The exemplary filters for distinguishing between minute defect scattered light and roughness scattered light are described above. However, the scattered light distribution on the pupil plane varies with the type of defect to be detected. Therefore, the light-shielding region 810 of the filter may be changed to match the type of defect.

Further, a polarization filter or a polarizer may be combined with the filter 112 to change the polarization direction or transmit only light oriented in a particular polarization direction depending on the position on the pupil plane 110. More specifically, the filter described in Patent Literature 1 may be used.

FIG. 8A illustrates the roughness scattered light intensity distribution of radially polarized light that is obtained when the pupil plane 110 is filtered with the filter 801 shown in FIG. 7A. FIG. 8B illustrates the minute defect scattered light intensity distribution of radially polarized light that is obtained when the pupil plane 110 is filtered with the filter 801 shown in FIG. 7A. When compared with the intensity distribution of a radially polarized light component of scattered light described with reference to FIGS. 3A and 3C, the mask 810 shields light from the region 310 where the intensity of roughness scattered light is high. Meanwhile, the illumination incidence direction of the region 310 where the intensity of minute foreign matter (defect) scattered light is high is partly shielded from light by the mask 810, but the light is transmitted through the filter within a large region. Therefore, when scattered light intensity obtained by filtering the scattered light of radially polarized light is compared with scattered light intensity obtained without filtering the scattered light of radially polarized light, the result of comparison indicates that the scattered light intensity of filtered roughness scattered light is significantly lower than the scattered light intensity of unfiltered roughness scattered light.

Meanwhile, the scattered light intensity of filtered minute defect scattered light is lower than the scattered light intensity of unfiltered minute defect scattered light. However, the degree of minute defect scattered light intensity attenuation is smaller than the degree of roughness scattered light intensity attenuation. In the present example, the difference in the amount of scattered light intensity attenuation by filtering is used to distinguish defects from defect candidates (steps S414 and S415). Distinguishing between defects by comparing the scattered light intensity obtained by filtering with the scattered light intensity obtained without filtering will be described later with reference to FIG. 9B.

The method of identifying a position of a defect in accordance with the flowcharts of FIGS. 4C and 4D will now be described with reference to FIGS. 9A and 9B.

The method of identifying a position of a defect candidate in step S412 of the flowchart in FIG. 4B or 4D will be described with reference to FIG. 9A. FIG. 9A shows a graph obtained by plotting, with two axes, P- and S-polarized light intensities that are detected by the detector 115 at minute defect and roughness positions on the imaging plane. As mentioned earlier, the P-polarized light and S-polarized light on the imaging plane correspond to radially polarized light and azimuthally polarized light that are converted by the distribution wavelength plate 109.

As described with reference to FIGS. 3A to 3D, minute defects are high in radially polarized light (P-polarized light) intensity and low in azimuthally polarized light (S-polarized light) intensity. Therefore, pixels plotted in the lower right region of the graph represent defect candidates. An exemplary determination method is to set a P-polarized light intensity threshold value t1 and an S-polarized light intensity threshold value t2, perform a threshold value process on the presumption that the P-polarized light intensity is equal to or higher than t1 and that the S-polarized light intensity is equal to or lower than t2, and determine the position of a pixel having a scattered light intensity satisfying the set threshold values as a defect candidate. The brightness value of a pixel at each position may be used as the scattered light intensity.

When the method described in Patent Literature 2 is used, images formed in different polarization directions are separately captured. Therefore, light oriented in one polarization direction is separated from light oriented in another polarization direction, and multiple detectors are used to separately capture the images formed in the individual polarization directions. Consequently, the spatial pixel-to-pixel correspondence of the images formed in the individual polarization directions is not guaranteed so that the scattered light intensities at the same or nearby positions of the images formed in the individual polarization directions cannot be compared with each other. As a result, defect scattered light may not be made distinct.

Meanwhile, the method according to the present example uses the device described with reference to FIGS. 5A to 6B and FIG. 14 and makes it possible to capture images formed in the individual polarization directions with the spatial correspondence guaranteed. Therefore, the scattered light intensities at the same or nearby positions of images formed in the individual polarization directions can be compared in a guaranteed manner, and thus the defect scattered light can be made distinct.

A method of distinguishing defects in steps S114 and S115 of the flowcharts in FIGS. 4C and 4D by comparing scattered light intensity obtained when filtering is performed by the filter 112 with scattered light intensity obtained when no such filtering is performed will now be described with reference to FIG. 9B. FIG. 9B shows a graph obtained by plotting, with two axes, the P- and S-polarized light intensities of defect candidates that are obtained when filtering is performed by the filter 112.

Figure 9A:
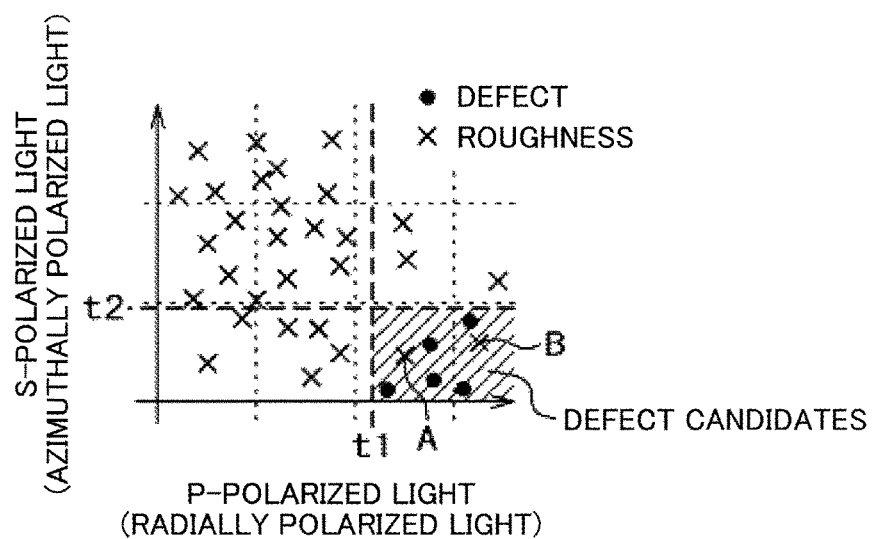
FIG. 9A is a graph illustrating the detection signal distribution of a P-polarized image and S-polarized image detected while no filter is disposed on the pupil plane.
Figure 9B:
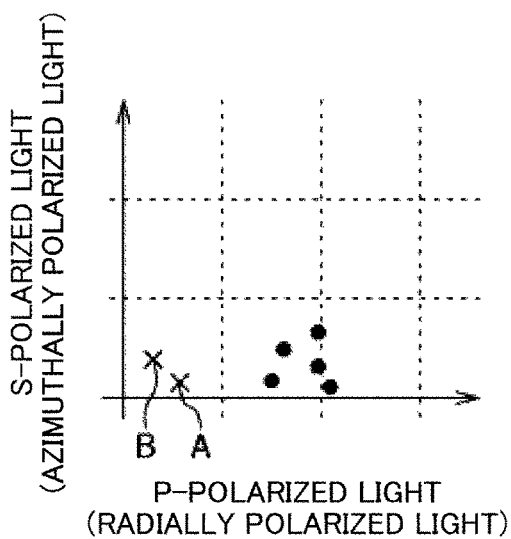
FIG. 9B is a graph illustrating the detection signal distribution of a P-polarized image and S-polarized image detected while a filter is disposed on the pupil plane.

Referring to FIGS. 9A and 9B, when P-polarized light (radially polarized light) intensity obtained when filtering is performed is compared with P-polarized light (radially polarized light) intensity obtained when no filtering is performed, the result of comparison indicates that, in the case of roughness scattered light received pixels, the intensity obtained when filtering is performed as indicated in FIG. 9B is significantly attenuated than the intensity obtained when no filtering is performed as indicated in FIG. 9A. Meanwhile, in the case of defect scattered light received pixels, the intensity obtained when filtering is performed as indicated in FIG. 9B is attenuated more than the intensity obtained when no filtering is performed as indicated in FIG. 9A. However, the degree of attenuation is smaller than in the case of roughness scattered light received pixels.

Defects can be distinguished, for instance, by calculating the amount of attenuation of P-polarized light and determining a pixel having an attenuation amount equal to or smaller than a threshold value t3 as a defect position. If there are multiple defect positions, all defect candidates having an attenuation amount equal to or smaller than the threshold value t3 can be outputted as defect positions, or a defect candidate having the smallest attenuation amount can be outputted as a defect position.

The attenuation amount of P-polarized light can be calculated, for instance, by letting p1 represent the brightness value of P-polarized light obtained when a defect candidate pixel is not filtered, letting p2 represent the brightness value of P-polarized light obtained when the defect candidate pixel is filtered, and substituting the values p1 and p2 into Equation 1.

Attenuation amount=$p1-p2$         (Equation 1)

Further, the brightness value of a minute defect that is obtained when the filter 112 is used for light shielding may be calculated by optical simulation, and a pixel having a brightness value equal to or greater than the simulated brightness value of a minute defect may be identified as a defect.

The method of decreasing the intensity of roughness scattered light by filtering in order to increase the difference from a defect to be detected has been described with reference to FIGS. 7A to 9B. However, the method is applicable when the intensity difference between roughness scattered light and defect scattered light can be increased. For example, a filter that significantly decreases the intensity of defect scattered light but slightly decreases the intensity of roughness scattered light may be used. An alternative is to use the filters 801 to 805 shown in FIGS. 7A to 7E with the light-shielding region 810 and the light-transmission region 811 interchanged. Further, when the type of defect to be detected is changed, the shape of the filter 112 or the polarization direction to be detected may be changed.

The threshold value process described with reference to FIGS. 9A and 9B may be performed by using a feature amount that is obtained by combining the individual polarized light intensities. For example, the differential value of each pixel of an image formed by P-polarized light and an image formed by S-polarized light may be used as the feature amount.

According to Patent Literature 1, the position of a defect is determined from one formed image derived from light that is obtained when the pupil plane is filtered with a filter. Meanwhile, the present example determines the position of a defect in accordance with the attenuation amount calculated from scattered light intensities that are obtained when filtering is performed and when no filtering is performed. As described with reference to FIGS. 9A and 9B, defect scattered light and roughness scattered light tend to exhibit different attenuation amounts. When the attenuation amount of a defect candidate is confirmed in a situation where the defect candidate cannot easily be identified by using only the information about a brightness value obtained after filtering by the filer 112 (that is, in a situation where, for example, a pixel has a high brightness value of roughness scattered light), it is possible to distinguish between defect scattered light and roughness scattered light. Consequently, the present invention provides an improved capability of distinguishing between defect scattered light and roughness scattered light.

In some cases, roughness scattered light received pixels indicated, for instance, by points A and B in FIG. 9A cannot be completely eliminated simply by performing a process as indicated in step S412 of FIGS. 4B and 4D. In such an instance, as indicated in steps S414 and S415 of FIG. 4D, a defect is identified by acquiring the P-polarized light intensity obtained when a defect candidate is filtered by the filter 112 and comparing the acquired P-polarized light intensity with the P-polarized light intensity obtained when no filtering is performed.

Figure 10:
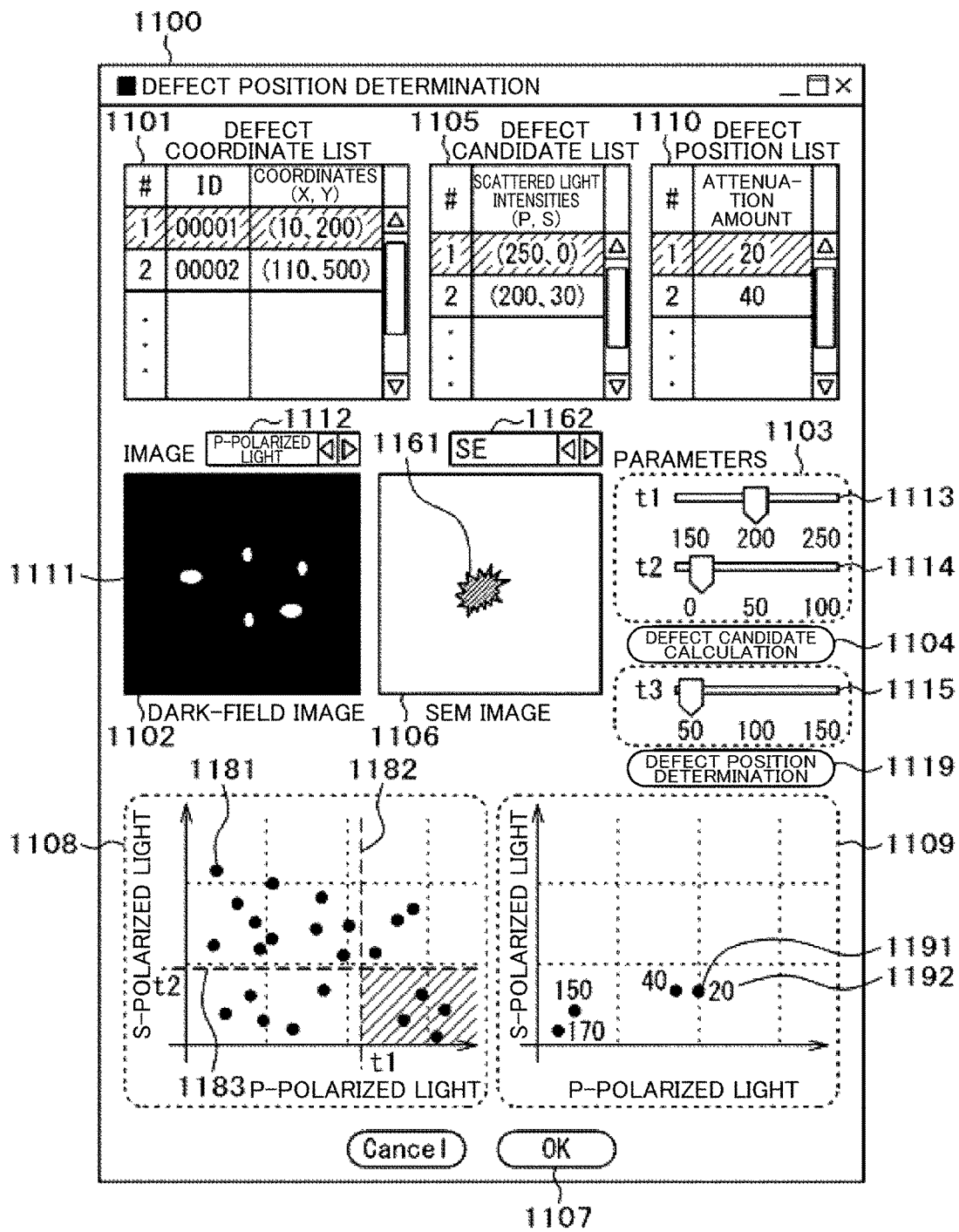
FIG. 10 is a diagram illustrating a GUI that displays the result of defect position determination according to an embodiment of the present invention and is used to set parameters for defect position determination.

A method of confirming the result of defect position determination and setting the threshold values will now be described with reference to FIG. 10. FIG. 10 illustrates an example of a graphical user interface (GUI) 1100 that is used to confirm the defect position determination result and set up parameters in accordance with the present example. The GUI 1100 appears on the display screen of the input/output unit 160 and accepts an input from a user.

The GUI 1100 displays a defect coordinate list display area 1101, a defect candidate list display area 1105, a defect position list display area 1110, a dark-field image display area 1102, an SEM image display area 1106, a parameter setup area 1103, a defect candidate calculation graph display area 1108, and a defect position determination graph display area 1109.

The defect coordinate list display area 1101 displays a list of defect candidates obtained from a defect inspection device. When the user selects a defect position candidate from a defect coordinate list displayed in the defect coordinate list display area 1101, the optical microscope 101 and the defect reviewing device are used to capture a dark-field image in accordance with the flowcharts shown in FIGS. 4B to 4D and display the captured dark-field image in the dark-field image display area 1102. The dark-field image display area 1102 displays an image formed by P- or S-polarized light that is captured by the detector 115 and selected from a list box 1112. The dark-field image display area 1102 may display an image obtained by combining images formed by P-polarized light and S-polarized light.

The defect candidate calculation graph display area 1108 displays a graph that shows, as described with reference to FIG. 9A, a P-polarized light brightness value along the horizontal axis and an S-polarized light brightness value along the vertical axis. Data points 1181 based on the brightness values of pixels are plotted and displayed. One data point 1181 may be plotted to represent each pixel or a group of neighboring pixels. When, for instance, a group of neighboring pixels is to be plotted, the average brightness value of the neighboring pixels may be plotted as a representative value. Displaying a group of neighboring pixels as one point decreases the number of plotted points in the graph in the defect candidate calculation graph display area 1108. This provides improved visibility.

Next, the user uses the slider bars 1113 and 1114 displayed in the parameter setup area 1103 in order to set parameters (threshold values t1 and t2) for defect candidate calculation, which have been described with reference to FIGS. 9A and 9B. The values t1 and t2 are the threshold brightness values of images formed by P-polarized light and S-polarized light, which are captured without using the filter 112 as described with reference to FIG. 9A. The values set by the slider bars 1113 and 1114 may be displayed in a graph in the defect candidate calculation graph display area 1108, for example, by using broken lines 1182 and 1183. Further, in order to obtain a setup reference, the user may, for example, click a data point to input coordinates of the data point, capture an SEM image at the inputted coordinates, and display the captured SEM image in the SEM image display area 1106.

The reference numeral 1161 denotes an SEM image of a defect. The SEM image may be captured by positioning the coordinates of the data point in the center of the SEM image or including the image of a surrounding area so as to include the coordinates of the data point. When the SEM image including the image of a surrounding area so as to include the coordinates of the data point is to be captured, for example, a dot or the x mark may be displayed at the coordinates of the data point in the SEM image in order to inform the user of the coordinates of the data point in the SEM image.

Further, the SEM image may be captured with the magnification changed to match the dimensions of a defect. This makes it easy for the user to confirm the defect. The dimensions of a defect can be estimated, for instance, by performing simulation based on the brightness value of coordinates of a data point in a captured dark-field image.

Moreover, the user may designate coordinates in the SEM image, for example, by clicking the mouse on the coordinates in order to capture the SEM image with the magnification of the designated coordinates raised or lowered and display the captured SEM image in the SEM image display area 1106.

The type of image to be displayed in the SEM image display area 1106 may be changed by a list box 1162 to a secondary electron image or a backscattered electron image. Whether the threshold values t1 and t2 are properly set can be determined by allowing the user to confirm an SEM image at a data point and check for defects.

Subsequently, when the user presses a defect candidate calculation button 1104, step S412 is performed based on the set parameters to calculate a defect candidate. The defect candidate is calculated by performing t1 and t2 threshold value processes on the brightness values of images formed by P-polarized light and S-polarized light, which are captured without the filter. The defect candidate list display area 1105 then displays information about the calculated defect candidate. The defect candidate list display area 1105 may display the defect candidate brightness values or coordinates of images formed by P-polarized light and S-polarized light, which are captured without the filter as indicated in FIG. 9A.

Further, the graph described with reference to FIG. 9B appears in the defect position determination graph display area 1109 at the press of the defect candidate calculation button 1104. The graph in the defect position determination graph display area 1109 shows a data point 1191 that is plotted by using the brightness values of defect candidate images that are formed by P-polarized light and S-polarized light and captured by using the filter. The attenuation amount described with reference to Equation 1 may be calculated for a defect candidate to display the attenuation amount 1192 of a spot in the vicinity of the data point 1191.

Next, a slider bar 1115 is used to set a parameter (threshold value t3) for defect position determination, which is described with reference to FIGS. 9A and 9B. The threshold value t3 is a threshold value for the amount of attenuation between the defect candidate brightness value of an image formed by P-polarized light and captured without the filter and the defect candidate brightness value of an image formed by P-polarized light and captured with the filter. When the attenuation amount calculated by Equation 1 is equal to or smaller than the threshold value t3, the associated defect candidate is identified as a defect position. In this instance, in order to obtain a t3 setup reference, the user may, for example, click a data point in the graph in the defect position determination graph display area 1109 to input coordinates of the data point, capture an SEM image at the inputted coordinates, and display the captured SEM image in the SEM image display area 1106. Whether the threshold value t3 is properly set can be determined by allowing the user to confirm an SEM image at a data point displayed in the SEM image display area 1106 and check for defects.

Subsequently, when a defect position determination button 1119 is pressed, steps S414 and S415 are performed based on the set threshold value t3 to determine a defect position and display the determined defect position in the defect position list display area 1110. The defect position list display area 1110 may display the attenuation amount and coordinates of the determined defect position and the brightness values of images formed by P-polarized light and S-polarized light that are obtained when the filter is used.

The defect position displayed in the defect position list display area 1110 is determined from a defect candidate displayed in the defect candidate list display area 1105. Therefore, the defect position list displayed in the defect position list display area 1110 may be linked with the defect candidate list displayed in the defect candidate list display area 1105 so that a defect position or defect candidate associated with a defect candidate or defect position selected in one of the two lists is selected from the other list.

Further, the list displayed in the defect position list display area 1110 may be identical with the list displayed in the defect candidate list display area 1105. In such an instance, while defect candidates are displayed, for example, the background color for a defect candidate determined as a defect position may be changed to notify the user of the defect position.

After the parameters are set for defects displayed in the defect coordinate list display area 1101 so as to obtain appropriate results in the defect position list displayed in the defect position list display area 1110, the user presses an OK button 1107 to terminate parameter setup.

When, for example, the user clicks a result displayed in the defect candidate list display area 1105 or the defect position list display area 1110 or a data point in a graph displayed in the defect candidate calculation graph display area 1108 or the defect position determination graph display area 1109, a selected position within an image displayed in the dark-field image display area 1102 may be, for example, enclosed by a square to highlight an associated defect position 1111.

As regards the lists displayed in the defect candidate list display area 1105 and the defect position list display area 1110, defect candidates and defect positions may be rearranged in ascending or descending order in accordance with information about attenuation amounts and scattered light intensities in the individual polarization directions.

The process performed at the press of the defect candidate calculation button 1104 and the process performed at the press of the defect position determination button 1119 may be performed collectively. When a relevant button is pressed in such an instance, data points, defect candidates, and defect positions are displayed, based on the t1, t2, and t3 settings, in the defect candidate list display area 1105, in the defect position list display area 1110, in the defect candidate calculation graph display area 1108, and in the graph displayed in the defect position determination graph display area 1109.

The parameters may be set by allowing the user to teach about a defect or false information instead of permitting the user to manipulate the slider bars 1103, 1114, 1115. Teaching may be conducted, for example, by allowing the user to select a defect candidate listing displayed in the defect candidate list display area 1105, permitting the user to click the mouse on a dark-field image displayed in the dark-field image display area 1102, or allowing the user to click a data point in a graph displayed in the defect candidate calculation graph display area 1108 or the defect position determination graph display area 1109.

FIG. 11 illustrates an exemplary configuration of a defect reviewing device 1200 in which the optical microscope 101 (FIG. 1) according to the present invention is mounted for coordinate alignment. The defect reviewing device 1200 according to the present embodiment includes a wafer holder 105, a scanning electron microscope (SEM) 1201, an optical height detection system 1211, an optical microscope 101, a vacuum chamber 1202, a stage 104, a control unit 1240, an input/output unit 1260, a storage unit 1250, a computation unit 1230, an image processing unit 1220, and a network 1204. The wafer holder 105 is a holder in which a wafer 103 to be inspected is mounted. The SEM 1201 is used to review the details of the wafer 103. The optical height detection system 1211 detects the surface height of the wafer 103 in order to focus the SEM 1201 on the surface of the wafer 103. The optical microscope 101 optically detects a defect on the wafer 103 and acquires detailed position information about the defect on the wafer 103. The vacuum chamber 1202 houses the objective lenses of the SEM 1201 and the optical microscope 101. The stage 104 on which the wafer 103 is mounted is positioned in the vacuum chamber 1202 and capable of moving between the SEM 1201 and the optical microscope 101. The control unit 1240 controls the SEM 1201, the optical height detection system 1211, the optical microscope 101, and the stage 104. The network 1204 connects to a host system such as an external inspection device 1203.

The SEM 1201 includes an electron beam source 1212, an extraction electrode 1213, a condenser lens electrode 1218, a deflection electrode 1214, an objective lens electrode 1215, a secondary electron detector 1217, and a backscattered electron detector 1216. The extraction electrode 1213 extracts primary electrons emitted from the electron beam source 1213 as a beam and accelerates the extracted primary electrons. The condenser lens electrode 1218 narrows the primary electron beam that is extracted and accelerated by the extraction electrode 1213. The deflection electrode 1214 controls the trajectory of the primary electron beam that is narrowed by the condenser electrode 1218. The objective lens electrode 1215 operates so that the primary electron beam whose trajectory is controlled by the deflection electrode converges on the surface of the wafer 103. The secondary electron detector 1217 detects the secondary electrons generated from the wafer 103 that is irradiated with the primary electron beam that is converged with its trajectory controlled. The backscattered electron detector 1216 detects relatively high-energy electrons such as backscattered electrons generated from the wafer 103 that is irradiated with the converged primary electron beam.

The stage 104, the optical height detection system 1211, the optical microscope 101, the SEM 1201, the input/output unit 1260, the storage unit 1250, the image processing unit 1220, and the computation unit 1230 are connected to the control unit 140. The control unit 140 is connected to the host system (for example, the inspection device 1203) through the network 1204.

The display screen of the input/output unit 1260 displays the GUI that is described with reference to FIG. 10. The image processing unit 1220 is configured as described with reference to FIG. 6C. The computation unit 1230 includes the signal comparative computation unit 131 and the defect position calculation unit 132, which have been described with reference to FIG. 1.

In the defect reviewing device 1200 configured as described above, particularly, the optical microscope 101 has a function of re-detecting a defect on the wafer 103, which is detected by the other inspection device 1203, by using the position information about the defect, which is detected by the other inspection device 1203; the optical height detection system 1211 has a primary electron beam focusing function of converging the primary electron beam of the SEM 1201 to the surface of the wafer 103; the control unit 1240 has a position correction function of correcting the position information about a defect, which is inspected and detected by the other inspection device 1203 in accordance with the position information about a defect detected by the optical microscope 101; and the SEM 1201 has a function of reviewing a defect whose position information is corrected by the control unit 1240. The stage 104 with the wafer 103 mounted on it moves between the optical microscope 101 and the SEM 1201 so that a defect detected by the optical microscope 101 can be reviewed by the SEM 1201.

The optical microscope 101 may be replaced by the optical microscope 1301, which has been described with reference to FIG. 13, or replaced by the optical microscope 1501, which has been described with reference to FIG. 14.

The defect position determination and image capturing processes for defect reviewing, which have been described with reference to FIGS. 4A to 9B, are performed by the defect reviewing device 1200 shown in FIGS. 1 and 11 in a manner described below with reference to FIGS. 12A and 12B.

FIG. 12A is an exemplary flowchart illustrating how a defect is imaged to review the defect in accordance with the present invention.

First of all, the wafer to be reviewed is loaded onto the stage 104 shown in FIG. 1 (step S1201). Next, the defect position information about defects, which is detected beforehand by the other inspection device 1203, is read into the storage unit 1250 through the network 1204 and the control unit 1240 (step S1202). M (M>1) defects to be reviewed are then selected from the defect position information (step S1203). The computation unit 1230 may execute a prepared program to select the defects. An alternative is to let the user select the defects through the input/output unit 1260.

Next, a bright-field optical microscope (not shown) is used to align the wafer 103 (step S1204). More specifically, the coordinates formed on the wafer 103 use a known positioning mark (alignment mark) to associate the wafer coordinates with stage coordinates in order to position target defect coordinates within the FOV of the SEM 1201 and at the center of the field of view of the optical microscope 101 when the stage 104 moves in accordance with the defect position information written with the coordinates on the wafer 103. The result of the above association is stored in the storage unit 1250 as the alignment information.

Next, the defect position information about defects, which is detected by the other inspection device 1203, is corrected for defects 1 to M, which are selected as review targets. First of all, defect m is moved into the field of view of the optical microscope 101 (step S1206). More specifically, defect m is moved by driving the stage 104 through the control unit 1240 after the stage coordinates of defect m are calculated by the computation unit 1230 from the defect position information about defects, which is detected by the other inspection device 1203 and stored in the storage unit, and from the alignment information acquired in step S1204.

After the stage 104 is completely moved, the position of defect m is determined (step S1207) by a method described later with reference to FIG. 12B, and the determined defect position is stored as corrected defect position m (step S1208). Next, m is replaced by m+1 (step S1209), and the resulting new m (m+1) is compared with preset M (step S1210). If m is equal to or smaller than M (if the query in step S1210 is answered "YES"), processing returns to step S1206. Steps S1206 to S1210 are then repeated for defects m (m=1, . . . , M).

After the corrected defect positions m of all defects m (m=1, . . . , M) are acquired (if the query in step S1210 is answered "NO"), m is set to 1 (step S1211). The corrected defect positions m are then used to sequentially move defects m into the FOV of the SEM 1021 (step S1212), and the SEM images of defects m are captured (step S1213). Next, m is incremented by one (step S1214), and the resulting new m is compared with preset M (step S1215). If m is equal to or smaller than M (if the query in step S1215 is answered "YES"), processing returns to step S1212. If multiple defect positions are determined for one defect m in step S1207, steps S1212 to S1215 may be repeated as needed to handle all the determined defect positions.

After the SEM images of all defects are captured (if the query in step S1215 is answered "NO"), the wafer is unloaded (step S1216) to terminate the process.

FIG. 12B is an exemplary detailed flowchart illustrating a process (step S1207) of identifying a defect with the optical microscope. First of all, setup is performed through the filter control unit 141 so that the filter 112 does not filter the pupil plane 110 (step S1231). This setup may be performed by physically moving the filter 112 away from the pupil plane through the use of the filter holder 111. When, for example, a DMD or liquid crystal is used as the filter 112, an alternative is to exercise control so that scattered light generated from the wafer 103 is transmitted through the whole region of the filter 112.

Next, images formed by P-polarized light and S-polarized light are captured with the optical microscope 101 (step S1232). The images formed by P-polarized light and S-polarized light can be separately captured by using a method described with reference to FIGS. 5A to 5C, FIGS. 6A to 6C, or FIGS. 15A to 15C. The captured images, which are formed by P-polarized light and S-polarized light, are stored in the storage unit 1250 (150) through the control unit 1240 (140).

The images formed by P-polarized light and S-polarized light, which are stored in the storage unit 1250 (150), are inputted to the signal comparative computation unit 131 in the computation unit 1230 (130) through the control unit 1240 (140). The signal comparative computation unit 131 examines each pixel by comparing the brightness value of the image formed by P-polarized light and the brightness value of the image formed by S-polarized light with the threshold value t1 and the threshold value t2. The result of comparison is inputted to the defect position calculation unit 132, and a pixel whose brightness value of the image formed by P-polarized light is not smaller than t1 and whose brightness value of the image formed by S-polarized light is not greater than t2 is selected as a defect candidate (step S1233). The selected defect candidate is stored in the storage unit 1250 (150) through the control unit 1240 (140).

Subsequently, setup is performed through the filter control unit 141 so that the filter 112 filters the pupil plane 110 (step S1234). This setup may be performed by physically moving the filter 112 onto the pupil plane through the use of the filter holder 111. When, for example, a DMD or liquid crystal is used as the filter 112, an alternative is to exercise control so that a light-shielding region is set for the filter 112.

Next, images formed by P-polarized light and S-polarized light are captured with the optical microscope 101 (step S1235). The images formed by P-polarized light and S-polarized light can be separately captured by using a method described with reference to FIGS. 5A to 5C or FIGS. 6A to 6C. The captured images, which are formed by P-polarized light and S-polarized light, are stored in the storage unit 1250 (150) through the control unit 1240 (140).

The image formed by P-polarized light (an unfiltered image formed by P-polarized light), which is captured in step S1232 and stored in the storage unit 1250 (150), and the image formed by P-polarized light (a filtered image formed by P-polarized light), which is captured in step S1235, are inputted to the signal comparative computation unit 131 through the control unit 1240 (140), and used to calculate the amount of attenuation in the brightness value of each pixel (step S1236). The attenuation amount may be calculated, for instance, from Equation 1. The calculated attenuation amount is stored in the storage unit 1250 (150) through the control unit 1240 (140).

Finally, the attenuation amount calculated in step S1236, which relates to the defect candidate selected in step S1233 and stored in the storage unit 1250 (150), is inputted to the defect position calculation unit 132 through the control unit 1240 (140), and a defect candidate pixel having an attenuation amount of not greater than t3 is determined as a defect position (step S1237). The determined defect position is then stored in the storage unit 1250 (150). Steps S1231 to S1237, which have been described above, correspond to the steps of the flowchart in FIG. 4D. If, in step S1237, multiple pixels are determined as defect positions, all such pixels may be stored as defect positions or a pixel having the smallest attenuation amount may be stored as a defect position.

The defect candidate acquired in step S1233 may be stored in the storage unit 1250 (150) as a defect position. In such an instance, steps S1234 to S1237 are not performed (the steps to be performed correspond to the steps of the flowchart in FIG. 4B). Alternatively, step S1232 and steps S1234 to S1237 may be performed for all or some pixels to determine defect positions without performing steps S1231 and S1233 (the steps to be performed correspond to the steps of the flowchart in FIG. 4C).

As described above, while defects are detected by an inspection device, minute defects that are previously obscured by roughness scattered light and undetectable can now be made distinct. When the above-described optical detection system is mounted in an SEM defect reviewing device to perform an SEM review at a defect position determined upon optical detection, a defect can be surely positioned within the FOV of an SEM. Consequently, when an image of a defect detected by the inspection device is reviewed by the SEM, the image can be automatically captured at a high success rate.

While the present invention has been described in detail with reference to embodiments, it is to be understood that the present invention is not limited to the above-described embodiments and that various changes and modifications may be made by those of ordinary skill in the art without departing from the spirit and scope of the present invention.

REFERENCE SIGNS LIST 100, 1200 . . . Defect reviewing device,
101, 1301, 1501 . . . Optical microscope,
103 . . . Wafer,
104 . . . Stage,
106 . . . Objective lens,
109 . . . Distribution wavelength plate,
110 . . . Pupil plane,
112 . . . Filter,
113 . . . Imaging lens,
114 . . . Imaging optical system,
115, 1512 . . . Detector,
120, 1220 . . . Image processing unit,
130, 1230 . . . Computation unit,
131 . . . Signal comparative computation unit,
132 . . . Defect position calculation unit,
140, 1240 . . . Control unit,
141 . . . Filter control unit,
150, 1250 . . . Storage unit,
160, 1260 . . . Input/output unit.

The invention claimed is:

1. A defect reviewing device comprising:
a dark-field microscope that includes:
an illumination light source that illuminates a sample with illumination light,
an objective lens that collects scattered light generated from the sample illuminated with the illumination light from the illumination light source,
a wavelength plate that converts polarization directions of the scattered light from the sample, the scattered light being collected by the objective lens,
a filter that selectively blocks part of the scattered light transmitted through the wavelength plate and transmits a remaining portion of the scattered light,
an imaging lens that forms an image of the scattered light transmitted through the filter, and
a detector that captures the image of the scattered light formed by the imaging lens;
a scanning electron microscope (SEM);
a table that carries the sample between the dark-field microscope and the SEM; and
a control unit that is communicatively coupled to the dark-field microscope, the SEM, and the table, wherein a processor of the control unit:
causes the table to move the sample to the dark-field microscope,
removes the filter to allow radially polarized light and azimuthally polarized light to be transmitted,
captures, using the detector, first images formed by the radially polarized light and the azimuthally polarized light with the filter removed,
replaces the filter,
captures, using the detector, second images formed by the radially polarized light and the azimuthally polarized light with the filter replaced,
determines a position of the defect on the sample by comparing the first images and the second images,
causes the table to move to the sample to the SEM, and
captures, using the SEM, SEM images of the defect based on the position of the defect determined.

2. The defect reviewing device according to claim 1, wherein the detector includes two-dimensionally arrayed pixels; and wherein neighboring pixels of the two-dimensionally arrayed pixels detect light beams polarized in different directions.

3. The defect reviewing device according to claim 1, wherein the wavelength plate further:
converts the radially polarized light and the azimuthally polarized light to different beams of linearly polarized light.

4. The defect reviewing device according to claim 1, wherein the processor further:
calculates a defect candidate by performing a threshold value process on a brightness values of images in different polarization directions.

* * * * *